US008150636B2

(12) United States Patent
Labarbe et al.

(10) Patent No.: US 8,150,636 B2
(45) Date of Patent: Apr. 3, 2012

(54) SYSTEM AND METHOD FOR TIME CORRELATED MULTI-PHOTON COUNTING MEASUREMENTS

(75) Inventors: Rudi Labarbe, Cardiff (GB); Roger Sewell, Cambridge (GB); Sam Pumphrey, Cambridge (GB)

(73) Assignee: GE Healthcare UK Limited, Little Chalfont (GB)

( * ) Notice: Subject to any disclaimer, the term of this patent is extended or adjusted under 35 U.S.C. 154(b) by 0 days.

(21) Appl. No.: 10/498,439

(22) PCT Filed: Dec. 6, 2002

(86) PCT No.: PCT/GB02/05543
§ 371 (c)(1),
(2), (4) Date: May 9, 2005

(87) PCT Pub. No.: WO03/050518
PCT Pub. Date: Jun. 19, 2003

(65) Prior Publication Data
US 2005/0256650 A1   Nov. 17, 2005

(30) Foreign Application Priority Data
Dec. 11, 2001   (GB) .................................. 0129589.8

(51) Int. Cl.
*G01N 21/64* (2006.01)
*G01N 31/00* (2006.01)
(52) U.S. Cl. ....................................... 702/22; 250/459.1
(58) Field of Classification Search .................. None
See application file for complete search history.

(56) References Cited

U.S. PATENT DOCUMENTS

| 4,686,371 | A |   | 8/1987 | Birch et al. |
|---|---|---|---|---|
| 5,459,323 | A |   | 10/1995 | Morgan |
| 5,851,488 | A | * | 12/1998 | Saul et al. ........................ 422/67 |
| 5,990,484 | A |   | 11/1999 | Ohsuka |
| 6,137,584 | A |   | 10/2000 | Seidel et al. |
| 6,297,506 | B1 | * | 10/2001 | Young et al. ................... 250/369 |

FOREIGN PATENT DOCUMENTS

| GB | 2162943 A | 2/1986 |
|---|---|---|
| GB | 2330904 A | 5/1999 |
| JP | 2000-304697 | 11/2000 |

OTHER PUBLICATIONS

Shimizu et al. "Development of a Time-of-Flight Positron Imaging System," IMTC (1994), pp. 1361-1364.*
McLoskey et al., "Multiplexed single-photon counting. I. A time-correlated fluorescence lifetime camera," Rev. Sci. Instrum., vol. 67 (1996), pp. 2228-2237.*
Hill, "Bayesian event reconstructio and background rejection in neutrino detectors," <http://arxiv.org/PS_cache/astro-ph/pdf/0106/0106081v1.pdf>.*
Aspnes et al., "Methods for drift stabilization and photomultiplier linearization for photometric ellipsometer and polarization," Rev. Sci. Instrum., vol. 49 (1978), p. 291-297.*
Hill, "Bayesian event reconstructio and background rejection in neutrino detectors," [2001] <http://arxiv.org/PS_cache/astro-ph/pdf/0106/0106081v1.pdf>.*
Alnis et al., "Sum-frequency generation with a blue diode laser for mercury spectroscopy at 245 nm," Applied Physics Letter, vol. 6 (2000) pp. 1234-1236.*
Ohsuka et al., "Time-correlated photon counting technique robust against multiple photon events using a multianode photomultiplier tube," Review of Scientific Instruments, vol. 71 (2000) pp. 354-360.*
Donohue et al., "Correction of Single Photon or Particle Timing Measurements for Multiple Events," The Review of Scientific Instruments, vol. 43 (1972) pp. 791-796.*
Davis et al., "Correction methods for photon pile-up in lifetime determination by single-photon counting," J. Phys. A: Gen. Phys., vol. 3 (1970) pp. 101-109.*
Whittenburg, S. L., "Bayesian analysis of biexponential time-decaying signals" Spectrochimica Acta Part A, vol. 54, 1998 pp. 559-566.
Suhling, K., et al., "Multiplexed single-photon counting II. The statistical theory of time-correlated measurements" Rev. Sci. Instrum., vol. 67, No. 6, Jun. 1996, pp. 2238-2246.

* cited by examiner

*Primary Examiner* — Marjorie Moran
*Assistant Examiner* — Anna Skibinsky

(57) ABSTRACT

The invention provides a method and a measurement system for characterization of luminescence properties, the method comprises irradiating the luminescent material with a pulse of excitation light, providing a triggering signal correlated to the pulse of excitation light; detecting with a photodetector such as a photomultiplier tube (PMT) a plurality of photons emitted from the luminescent material as result of the pulse of excitation light, the photodetector providing an output signal upon the event of detection of a photon; determining for each detected photon a photon arrival time and providing an output suitable for inputting to an analysing module wherein an output comprises zero, one, or more photon arrival time for each excitation, receiving said outputs in an analysing module; and determining in the analysing module, characteristics properties of the luminescent material by performing a statistical analysis based on Bayesian inference.

11 Claims, 7 Drawing Sheets

SYSTEM AND METHOD FOR TIME CORRELATED MULTI-PHOTON COUNTING MEASUREMENTS

CROSS REFERENCE TO RELATED APPLICATIONS

This application is a filing under 35 U.S.C. §371 and claims priority to international patent application number PCT/GB02/05543 filed Dec. 6, 2002, published on Jun. 19, 2003 as WO 03/050518 and also claims priority to patent application number 0129589.8 filed in Great Britain on Dec. 11, 2001; the disclosures of which are incorporated herein by reference in their entireties.

The present invention relates to a method and system for measuring luminescence lifetime. More particularly, the invention relates to a method and apparatus that significantly reduces the measurement time in a Time Correlated Multi-Photon Counting (TCMPC)-measurement.

BACKGROUND OF THE INVENTION

Measurement of the luminescence emission of substances has become increasingly important as a sensitive analytical technique in a wide range of disciplines such as chemistry, biology, engineering, materials science and application areas ranging from pollution monitoring and production control in a chemical plant to the sequencing of DNA. In many of these areas, distinguishing the weak but characteristic emission of the substance of interest from background light is difficult. Measuring the lifetime of the light emission of the substance of interest can often be used to discriminate the desired signal from a background. In this context we define the luminescence lifetime of a substance to be the time taken for the intensity of light emitted in response to an exciting pulse of light to fall to 1/e (~1/2.7) of its initial value. This characteristic time can range from less than one nanosecond to minutes, depending on the processes involved. Such processes can be described as fluorescence, luminescence or phosphorescence, but if the desired light emission has a lifetime which is different from light of another source, its detection can be enhanced.

One example of fluorescence measurements is in DNA sequencing, where molecular fragments are 'labelled' with a fluorescent dye and the fluorescence emission of a dye-labelled fragment is used to identify which amino acid base begins or ends a given sequence of amino acids. Another application is in the screening of potential drugs against a target molecule. Typically changes in fluorescence intensity are used to identify 'hits' in response to a chemical test or 'assay' of the interaction between a potential drug and a target molecule. In this case, either the drug or the target or both may be labelled. In both sequencing and screening, the characteristic lifetime of a fluorescent molecule can be used to improve its detection.

A fluorescent material is a material which can be excited to a higher electronic state and on relaxing towards its ground state emits a photon. The time elapsed from the excitation until the emission of a photon, the intensity of emitted photons, and the energy (frequency) of the photons are all properties that can be measured and used to characterize the material. The excited state is typically achieved by subjecting the material to a short light pulse. The emission of photons is a Poisson process and the intensity of the emitted photons is continuously decreasing, and typically follows an exponential decay. A useful way of characterising a fluorescent material is to measure the time elapsed between an excitation and the arrival of photons at a detector. $\lambda(t)$ denotes the Poisson arrival rate at time t at all times and is given by:

$$\lambda(t) = Ae^{-\alpha t} \qquad \text{equation 1}$$

where A denotes the intensity of a single fluorescent material, measured in photons per second, at time 0 (the time of the excitation), also referred to as the initial intensity, $\alpha$ denotes the decay constant of the fluorescence, measured in nepers/second, and $1/\alpha$ is the fluorescence lifetime, which is often used to characterise a fluorescent material. If a sample has more than one fluorescent material present, the arrival rate of photons can typically be described by a multiexponential expression.

A widely used technique of determining the fluorescence lifetime of a material is Time Correlated Single Photon Counting (TCSPC). In TCSPC a sample is typically subjected to a short light pulse, which excites the material in the sample. The material will, if fluorescent, emit a photon a short time after the excitation. The emitted photon is detected and the time that has elapsed between the excitation light pulse and the arrival of the first emitted fluorescence photon is recorded by the measurement system. The technique is only capable of counting a maximum of one photon per excitation. In practice less than one photon per excitation are counted since, to get a representative distribution of arrival times, a low intensity of the exciting light pulse is used, giving a low probability of photon emission. Therefore, to get a reliable measure of the fluorescence lifetime characteristic of a particular material, using TCSPC, i.e. to acquire a fluorescence decay curve, the process of exciting the material in the sample and detecting the first emitted photon, has to be repeated a large number of times. A measurement can typically involve several tens of thousands excitation-photon detection cycles. The TCSPC method has been continuously improved, for example U.S. Pat. No. 5,990,484 teaches a method and apparatus for counting a total number of emitted photons, allowing a higher intensity of the exciting light pulse, and U.S. Pat. No. 4,686,371 teaches a method of compensating for variations in the length and intensity of the exciting light pulse.

As above indicated, TCSPC can, even if the mentioned improvements are utilised, be a time consuming measurement. It is realised in the art that the method is wasteful in that only the first emitted photon is detected and used for the determination of the fluorescence lifetime, even though the subsequently emitted photons carry information useful for the determination of the characteristic lifetime. A number of approaches have been suggested to extend the TCSPC to also detect and record subsequent photons. The most recent development of the TCSPC-technique includes various multiplexing techniques, in which, in principle, a plurality of detectors are connected to one or more analysing means, examples described in Multiplexed single-photon counting by Scubling et al., Rev. Sci. Instrum. 67 (6), 2238-2246 June 1996. Alternatively multi-element detectors have been suggested, for example by Browne et al. in A 100 ns anti-coincidence circuit for multi-channel counting systems, Meas. Sci. Technol. 6 (6), 1487-1491, June 1996. The suggested Multiplexed Time Correlated Single-Photon Counting (M-TCSPC)—techniques represent significant improvements over the TCSPC—techniques, but have the drawback that the number of photons that it is possible to detect following one excitation pulse is limited by the number of detectors (or detector elements) used; therefore a large number of excitation cycles is still needed to determine the fluorescence lifetime of the material. In addition multielement detectors are costly, as are systems providing a large number of single detectors in a multiplexing arrangement.

The known apparatus and measurement techniques thus suffer, as above described, from a number of disadvantages and limitations, the most important being the long measurement time. Thus, there is a need in the art to provide a measurement system and method that shortens measurement time.

SUMMARY OF THE INVENTION

The object of the present invention is to provide a system and a method that significantly reduces the measurement time in a major part of the applications. The inventive system is defined in claim 10 and the method and corresponding software module in claims 1 and 9, respectively.

One advantage afforded by the present invention is to be able to use a limited dataset by using a Bayesian algorithm to make better use of the available data.

Yet another advantage of the invention is to be able to take into account the PMT dead time in the lifetime analysis or any other instrumental parameters, such as e.g. non-delta illumination, etc.

Yet another advantage of the invention is the possibility, as a result of a measurement, of giving the posterior probability distribution of a fluorescence lifetime and/or intensity in contrast to the prior art, which typically only gives a single value as a measure of the lifetime and/or intensity.

BRIEF DESCRIPTION OF THE DRAWINGS

The invention will now be described in detail with reference to the drawing figures, in which.

DETAILED DESCRIPTION OF THE INVENTION

Figure 1:
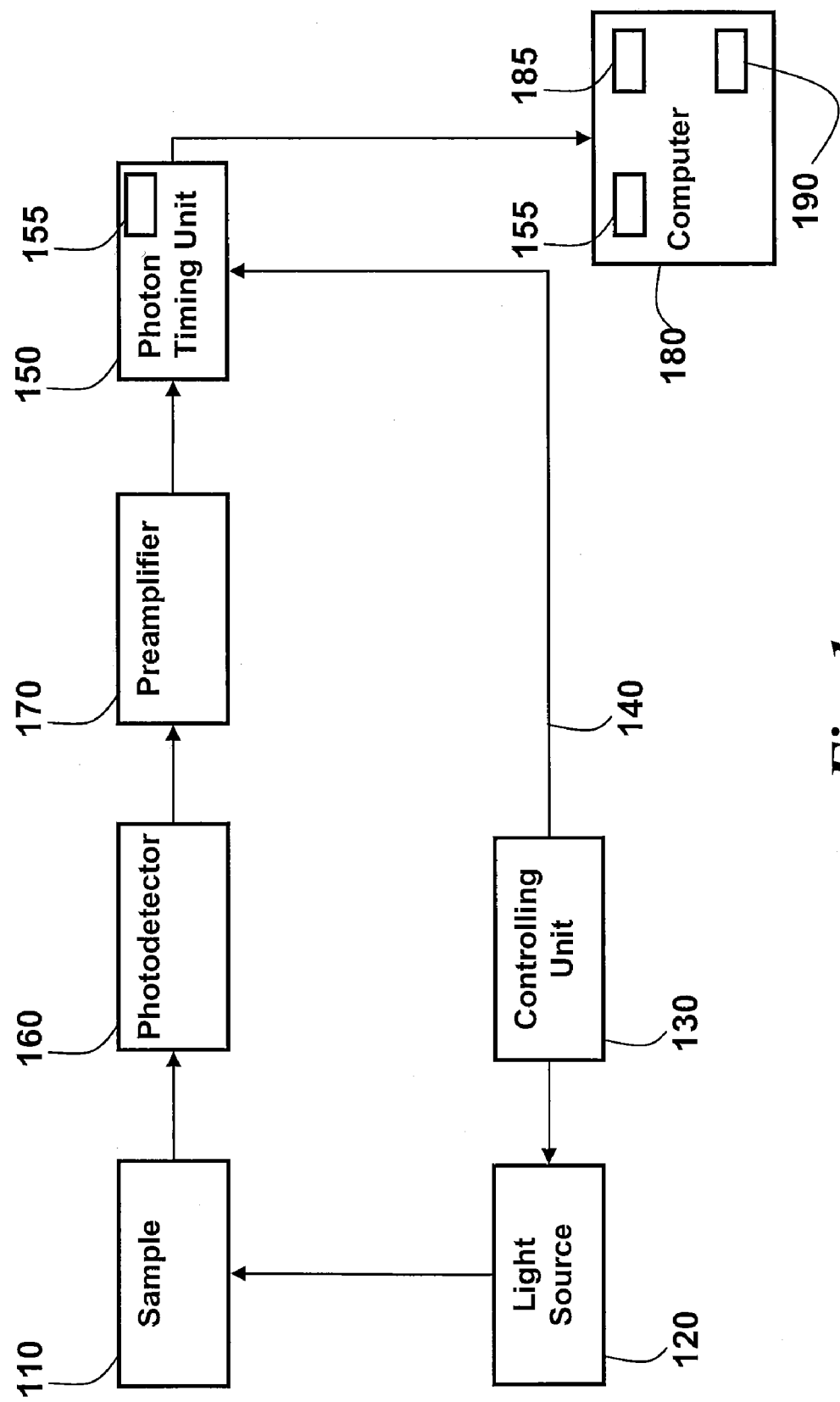
FIG. 1 is a schematic illustration of a single channel TCMPC system according to the invention.

The inventive measurement system provided by the present invention will be described with reference to the schematic illustrations of FIG. 1-2. FIG. 1 shows a single channel TCMPC system according to the invention. Fluorescent material is contained in a sample 110. An excitation light source 120 for repeatedly irradiating the sample with pulses of excitation light is provided. The light source preferably a pulsed laser. A light source driving and controlling unit 130 comprises the laser power supply and is arranged to generate a triggering signal 140 to a photon timing unit 150. The repetition rate of the excitation light should be sufficiently low to allow a total decay of the fluorescence of the sample before the next exciting pulse. A pulsing frequency of for example around 200 kHz would commonly be appropriate. The duration of the pulse of excitation light should be significantly shorter than the fluorescence lifetime of the fluorophore in order to obtain reliable lifetime measurements. A typical fluorophore has a fluorescence lifetime in the range of 1-100 ns and a suitable length of the light pulse would be in the order of 0.5 ns. The frequency of the pulse is an example of a parameters typically adjusted for the sample under investigation (the length of the light pulse is an intrinsic characteristic of the laser and typically cannot be easily changed). In addition, the light source 120 and the light source driving and controlling unit 130, should preferably have the facility to adjust other parameters such as the number of pulses and the intensity of the excitation light in order to account for e.g. the amount of fluorophore in the sample, the needed accuracy in the result etc. Light sources, e.g. pulsed lasers, with the characteristics described above and with driving and controlling units therefore are known in the art and commercially available; for example, the NanoLED-07 picosecond laser source from IBH.

Positioned adjacent to a sample chamber containing the sample 110 is a photodetector 160, which has the purpose of detecting the emitted fluorescent photons. Different optical components are placed between the sample and the detector. For example several lenses are used to maximise the amount of fluorescent light collected from the sample and to focus the light onto the detector. Furthermore dichroic mirrors and filters are used to select a range of wavelength and prevent the excitation light from reaching the detector and only let the light having a range of wavelength corresponding to the fluorescence spectrum of the fluorophore reach the detector. An optical component is also used to split the beam of the fluorescent light into several beams that are then directed to the different detectors. This splitting can be achieved in different ways, e.g. by using a beam splitter cube or by using multi-branch fibre optics. These are well known in the art and are commercially available (for example, from Oriel Instrument, 150 Long Beach Boulevard, Stratford, Conn., USA or from Melles Griot, St Thomas Place, Ely, Cambridgeshire, England). The photodetector preferably comprises a photon counting photomultiplier tube (PMT) but other detectors such as an avalanche photodiode can be used. The signal from the photodetector is typically amplified in a pre-amplifier 170. After amplification, the signal can go through a discriminator unit that remove the unwanted noise from the signal and only leave the electrical pulses generated by the photons on the PMT. The discriminator unit is then connected to the photon timing unit 150. The photon timing unit comprises for example a very fast analogue-to-digital converter (A/D converter) and a memory for storing datapoints. As discussed above, it should be possible for more than one photon per excitation, resulting from the excitation light pulse, to be recorded by the photodetector 160 and the photon timing unit 150, not only the first emitted photon as in the TCSPC based techniques. This put certain requirements on the photodetector 160 and the photon timing unit 150; A photon detected by the PMT will give rise to an output pulse that has a duration of c.a. 4-6 ns with the current technology. To identify a PMT pulse position in time at least 4-8 data points per pulse are needed, in accordance with the method described further below. In order to detect a plurality of such pulses the A/D converter needs to have a sampling frequency at least of around 2 GS/s and the ability to store data points corresponding to an acquisition period of approximately 100 ns. A/D converters with such extreme capabilities have only recently been made commercially available. An example of a suitable A/D converter is the Acquiris DP210 (2 GS/s) from Acquiris Europe, 18 chemin des Aulx, 1228 Plan-les-Ouates, Geneva, Switzerland. The collected data points are analysed by an arrival time determination module 155, preferably realised as a software program module residing either within the photon timing unit 150, or alternatively within an external computer 180, to determine the arrival time of the fluorescence photons. Examples of suitable algorithms for arrival time determination will be given below. Arranged to receive and analyse a dataset of photon arrival times from the arrival time determination module, is an analysing module 185, which preferably is a software program package implemented in and executed on the computer 180. The computer can be a general purpose computer such as a PC or a workstation or a special purpose machine. The computer 180 is preferably also used for controlling the measurements, monitoring the equipment etc. and therefore is equipped with communication means (not shown) connected to other units of the measurement system. Installed in and executing on the computer, is then also a software program module for measurement control 190. As appreciated by the skilled in the art, the installation of and execution of the software modules 155, 185 and 190 can be done in various ways and in various computer configurations. For example the measurement control unit 190 can be executed in a PC suitable for laboratory conditions, the arrival time determination module 155 can be incorporated within the photon timing unit, and the analysing module 185 in a special purpose machine designed for the high computational speed needed for certain analysis. The inventive methods utilised by the analysing module 185 will be described in detail below.

Photodetectors such as PMTs give a signal that typically last 4-5 ns. During that time the PMT is incapable of detecting any new photons. This is often referred to as PMT dead time. If photons arrive during the PMT dead time, i.e. less than 5 ns apart, the measurement system will not be able to record them. As will be described further below, the analysing method can be made to take into account the PMT dead time, but the fact that the system is incapable of recording photons during certain time intervals will prolong the needed measurement time.

In one embodiment of the present invention the measurement system has been provided with a plurality of photodetectors (PMT) and amplifiers connected to them, giving a multi-channel TCMPC. In FIG. 2 this is exemplified with a dual-channel system, having a first PMT 200, and a second PMT 205, connected to preamplifiers 210 and 215, respectively. The preamplifiers are connected to a common photon timing unit 150 with independent channels. Alternatively a plurality of photon timing units can be used. If one of the PMT is recovering after detecting a photon, the other may still be capable of detecting a subsequent photon. The effective dead time of the system is thus reduced. More than two PMT—amplifier channels can be used to further reduce the effective PMT dead time.

Figure 3:
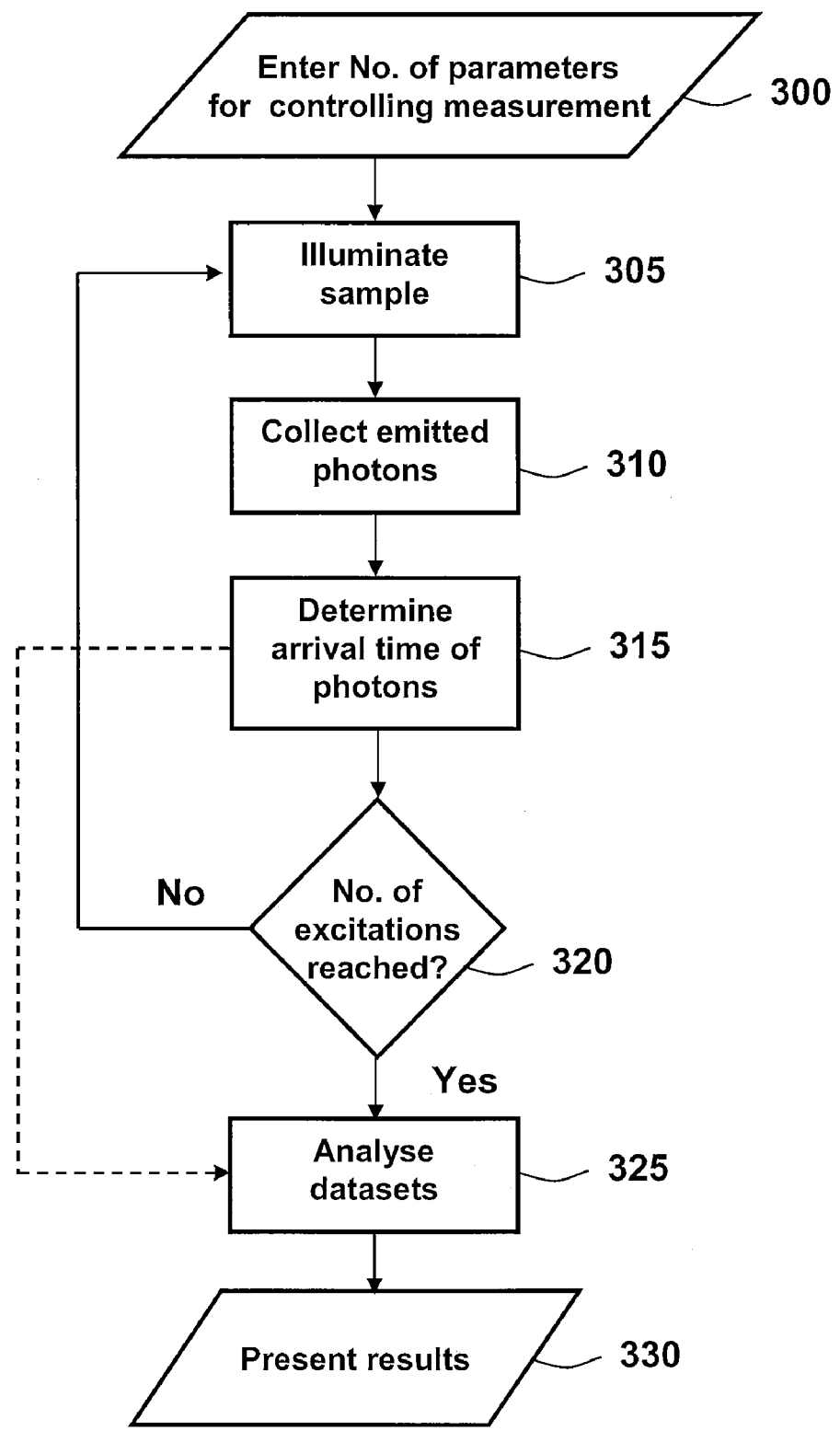
FIG. 3 shows a flowcharts of the measurement and analysing method according to the invention.

An experimental procedure using the inventive methods and measurement system according to the invention will be described with references to the flowchart of FIG. 3. Variations of the experimental procedure are possible and the procedure now described should be considered as one of many embodiments possible. The aim of the measurement is typically to determine the initial intensity of fluorescence, the fluorescence lifetime ($1/\alpha$) or the posterior probability distribution of the intensity or lifetime of one or a plurality of fluorophores contained in the sample 110.

The experimental procedure comprises:
  300: In a first step 300, the user enters, to the measurement controlling module 190 and the analysing module 185, a number of parameters used for controlling the measurement, choosing an appropriate analysis algorithm depending primarily on prior knowledge of the sample, and parameters describing the performance of the equipment such as PMT dead time. Parameters important for the inventive methods described below comprise:
    N—the number of excitations (laser pulses);
    $\alpha_i$—the reciprocal of the fluorescence lifetimes (if known) and/or the prior distribution of lifetimes, $P(\alpha_i)$;
    $A_i$—the fluorescence initial intensities (if known) and/or the prior distribution of intensities, $P(A_i)$;
    $\delta$—the PMT dead time;
    $\tau$—the time the detector is blocked after an excitation;
    $\upsilon$—the duration of recording after each excitation
    A1, A2, A3, A4, A5, A6, A7, A8—Analysis algorithms
    Many of the parameters are not changed for each measurement and default values are preferably stored in a database.
  305: The measurement starts by illuminating the sample 110 with a pulsed laser 120.
  310: In a next step, 310, the emitted photons are collected by PMT tube(s) 160 and the signal is amplified by a pre-amplifier 170 and possibly the signal is discriminated to remove unwanted noise.
  315: In step 315, the arrival time of the emitted photons are determined by the photon timing unit 150 and the arrival time determination module 155, with one of the methods that will be described below. The arrival time determination module 155 outputs for each excitation n a dataset $D_n$, comprising the photon arrival times, to the analyzing module 185.
  320: In step 320, if the predetermined number of excitations N is reached the procedure goes to step 325, if not, steps 300-320 are repeated.
  325: In step 325, the datasets $D_n$ are analysed with one (or more) of the algorithms A1-A8, the algorithms being based on Bayesian inference.
  330: In a final step 330, the result is presented to the user. Depending on the algorithm chosen and the preferences of the user the output can be distributions of the fluorophore lifetimes or initial intensities, joint distributions, a measure of a fluorophore lifetime etc.

Alternatively the measurement procedure can stop then a predefined accuracy is achieved. In this case the analysis using Bayesian inference (step 325) is performed within the main loop of the algorithm. If, for example, the measure of a fluorescence lifetime has the predefined accuracy, the loop is halted. The procedure can of course in addition have a limit to the number of pulses used, which terminates the measurement even if the specified accuracy has not been met.

Arrival Time Determination

Figure 4A:
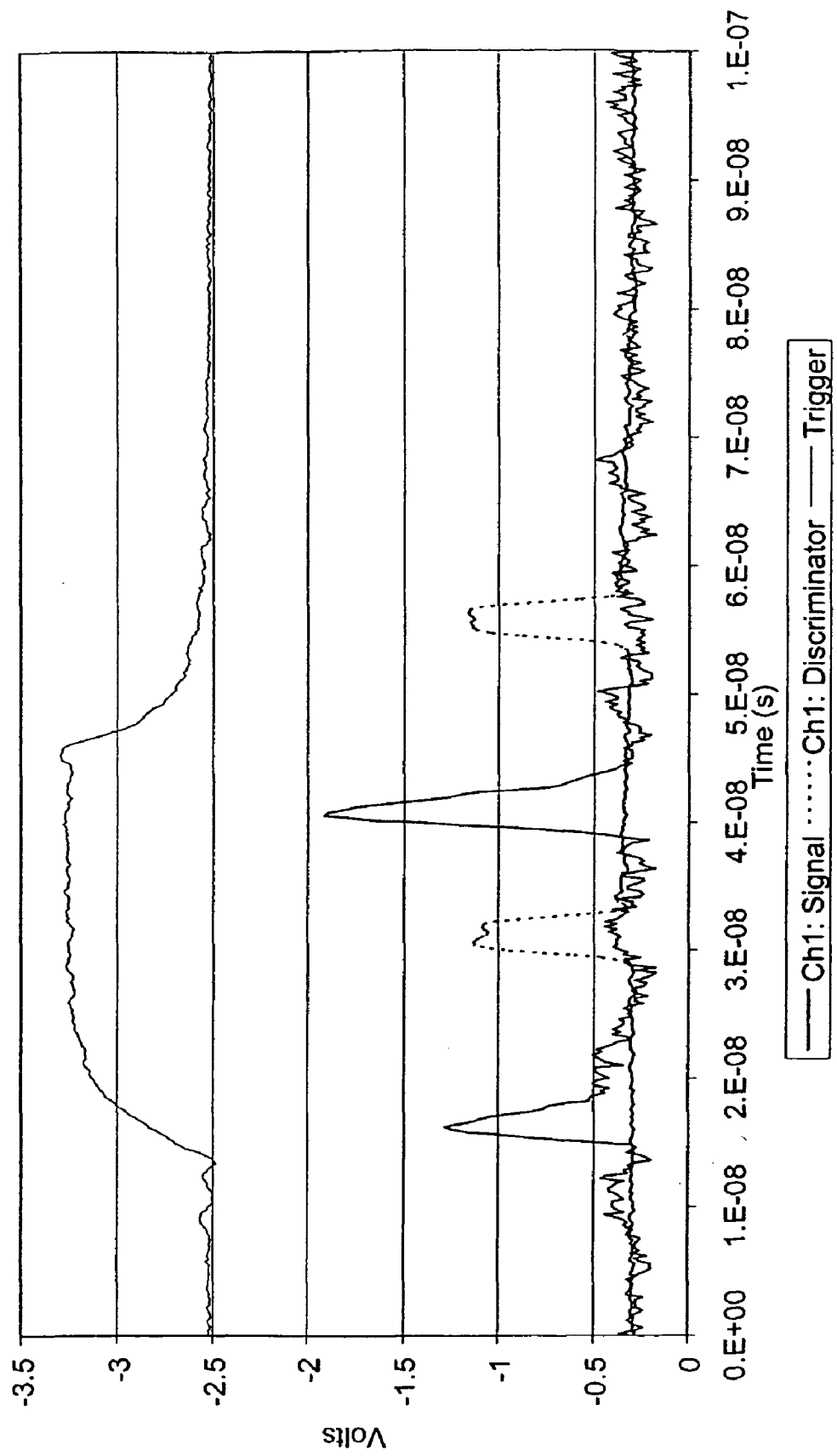
FIG. 4a is a graph showing an example of a trace from the photon timing unit.

The method of determining photon arrival times performed in the arrival time determination module 155, will be described with reference to FIG. 4 a-b. FIG. 4a gives an example of an output, commonly known as a trace, from the photon timing unit 150. The initial broad peak in the top curve corresponds to the triggering signal 140 sent from the light source driving and controlling unit 130 to the photon timing unit 150, when the excitation light source 110 irradiates the sample. It should be noted that this triggering signal itself is much longer (in this case it lasts for about 50 ns) than the actual laser pulse (that last for only 0.5 ns). Only the rising part of the signal is used by the photon timing unit 150 to determine the trigger to start the time base. The rest of the triggering signal is ignored by the photon timing unit. It must be noted that the length of the triggering signal does not correspond to the length of the laser pulse. If the laser pulse is longer than the resolution of the photon timing unit, one can block the photodetector during a time $\tau$. An emitted fluorescence photon is detected by the PMT and give rise to the pulse from the PMT, amplified in the pre-amplifier (solid line on FIG. 3), discriminated to remove the noise (dotted line on FIG. 3) and digitised in the A/D-converter, to show as the peak 210. It should be noted that the discriminator introduces a delay in the signal, explaining the shift between the position of the pulse in the solid and dotted line. This is not a problem, as this time delay is constant, it can be subtracted subsequently by the timing unit The time elapsed between the triggering signal and the appearance of the first peak 210 is the arrival time of the first fluorescence photon. The second peak 220 corresponds to a subsequent fluorescence photon.

A method of determining the arrival time of the fluorescence photons will now be described with references to FIG. 4 a-b. The trace is a list of data points, each point representing an output voltage from the PMT at a given time. In the embodiment with a plurality of photodetectors a corresponding plurality of parallel traces will result. In a first step 505 a zero time is defined as the beginning of the triggering pulse (for example, at the time when the trigger pulse reaches 50% of its maximum amplitude). The second step 510 is discrimination by selecting a part of the trace that is larger than a threshold value (this can be done by software or by hardware in the discriminator). In the following step 515 a local maximum of the voltage is defined as a point that is larger than both the point directly preceding it and the point directly following it. The time corresponding to the local maximum is recorded in step 520. This is defined as the arrival time of the photon. The method is preferably realised by a software program executed either in the photon timing unit 150 or in an external computer 180. The result is a dataset $D_n$ of measured arrival times for each excitation pulse n. As appreciated by the skilled in the art other methods of finding arrival times in a trace of datapoints can be utilised. For example, a first point larger than a preset threshold, or the point with the largest slope (largest derivative) in the peak, can be used to define an arrival time. The method chosen is typically a trade-off of the required precision in the definition of the arrival time and the computational time needed to determine the arrival time.

Figure 2:
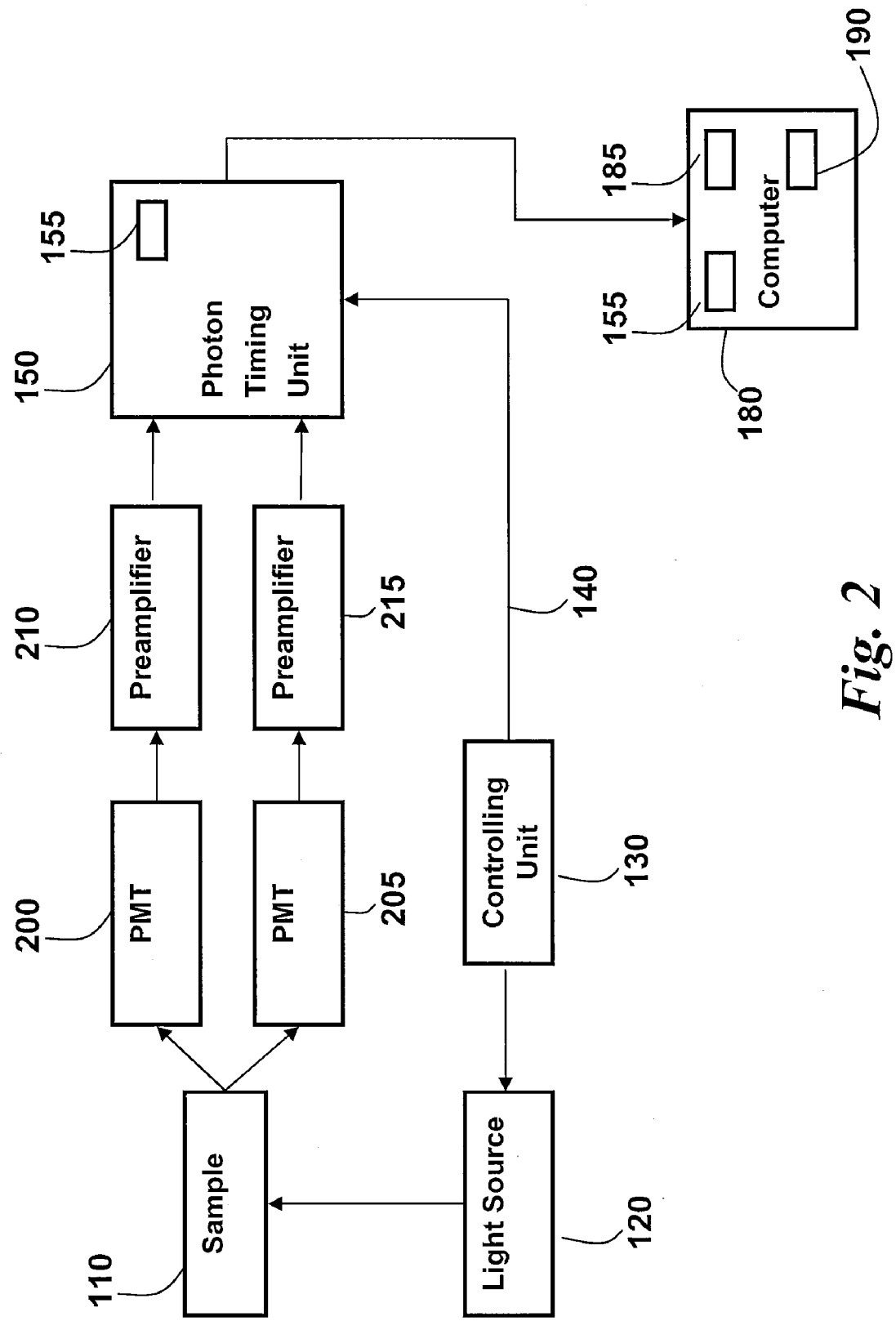
FIG. 2 is a schematic illustration of a multiple channel TCMPC system according to a preferred embodiment of the invention.
Figure 4B:
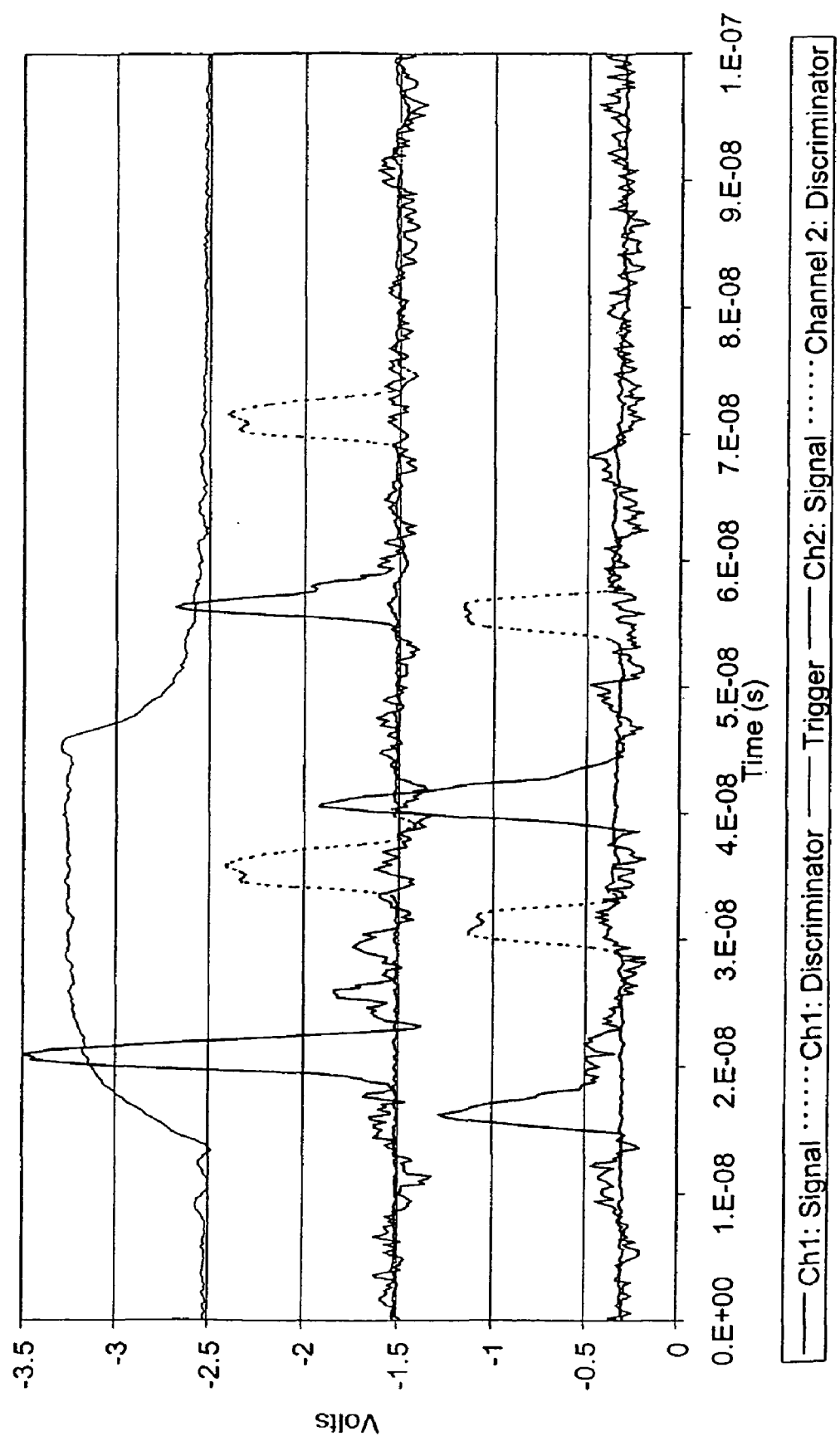
FIG. 4b is a graph showing an example of a trace from the photon timing unit from the multi-channel TCMPC system.

FIG. 4b shows the two traces, and the trigger signal from the laser pulse, resulting from the measurement system of FIG. 2. Both the multi-channel and the single-channel TCMPC can further be provided with discriminators, one for each channel, or other noise reduction means.

It should be noted that with all these methods, there is sometime an artefact. The algorithm may identify two points (or more) in a single pulse that satisfy the selection criteria. In order to remove the artefactual points, a subroutine would check whether several selected points are spaced with a time less than the PMT dead time and only select the first point in the group.

Bayesian Inference

The method of the present invention, which will be illustrated by the embodiments, algorithms A1-A8, are based on the principle of Bayesian inference. Bayesian inference offers a way of determining the (posterior) probability distribution of a variable (or vector of variables) in the light of some data taking into account prior knowledge of the probability of the variable taking various values. As an example, let us suppose that θ represents what we want to know. Usually θ will be a vector of many numbers; it might for example be the vector of intensities of a number of fluorophores. Let us suppose that D represents what we do know. D might for example the arrival times of some photons. Now, we know that for any specific value of θ, which specifies the vector of intensities, that some values of D are more likely and others less likely, and because we know the manner in which the data arises from θ, we can say exactly how much more or less likely. In other words, we can evaluate, for any specific values of θ and D, the value of P(D|θ), the probability of D given θ. We also know, before we even receive D, that some values of θ are more likely than others. For the photon counting example negative intensities can be excluded, as can values of the intensities that are extremely large (e.g. >1 e15 per second) or too small. This can all be precisely specified as a prior distribution on θ, denoted P(θ).

What we actually want to know is the value of θ, given some specific value of D. This is given by Bayes' theorem:

$$P(\theta | D) = \frac{P(\theta)P(D|\theta)}{\int P(\theta)P(D|\theta)d\theta} \quad \text{equation 2}$$

which tells us that given that particular value of D, how likely each value of θ is. In eq. 2 P(θ) is referred to as the Prior, P(D|θ) as the Likelihood, P(θ|D) as the Posterior, and ∫P(θ)P(D|θ)dθ as the Evidence (for the model).

A posterior distribution derived by Bayesian inference may by used in different ways: View the entire posterior distribution—possible in some cases (dimensionality not more than 2) and impossible in others; MAP (maximum a posteriori)—find the value of θ where the posterior probability density is greatest (if possible); and report just that value of θ, Mean posterior value—report the mean posterior value of θ, θθP(θ|D)dθ; Random samples—drawing random samples from the distribution P(θ|D). The method of random samples is often the preferred way of using the Posterior. Random samples can be independent or non-independent.

The Bayesian principles are utilized in the inventive method of the present invention for substantially shortening the measurement time needed for e.g. determination of a fluorescence lifetime. The reduction in measurement times arises from the fact that by using Bayesian inference adapted to the application of TCMPC fewer photons are needed to characterize a fluorophore compared to the prior art methods. The method fully utilizes the advantage afforded by the inventive system of detecting a plurality of photons for each excitation pulse. Depending on the prerequisite of the measurement, e.g. the number of different fluorophores present in the sample, different embodiments of the method will be appropriate, corresponding to the mentioned algorithms A1-A8. The algorithms are preferably comprised in the analysing module 185, as software programs implemented in and executed on the computer 180 (although it would be possible to embody them in other ways). In the measurement procedure outlined with references to FIG. 3, the programs based on the algorithms are addressed in the initialisation step 300 and the analysis step 325. A brief theoretical background will be given to each algorithm and the algorithms will be presented as pseudo-code with references to accompanying flowcharts.

Algorithm A1, Unknown Fluorophore Lifetimes, Single Fluorophore, No Deadtimes.

The decay rate of a single fluorophore is given by equation 1. To use Bayesian inference, we must have a prior distribution on the unknowns. We will use Gamma distributions on both A and α, as this is both sufficiently expressive and results in relatively simple mathematics. The Gamma distribution has two parameters, m, the shape parameter, and r, the scale parameter, both of which must be positive. Its probability density is given by $$\Gamma_{m,r}(x) = \frac{r^m x^{m-1} e^{-rx}}{\Gamma(m)} \text{ or for log } x : \Gamma_{m,r}(\log(x)) = \frac{r^m x^m e^{-rx}}{\Gamma(m)} \quad \text{Equation 3}$$

Varying r scales the whole distribution; varying m changes the shape of the distribution, allowing very broad distributions when m is small and very narrow ones when m is big. We can therefore choose appropriate parameters, and set $$P(A) = \frac{r_A^{m_A} A^{m_A-1} e^{-r_A A}}{\Gamma(m_A)} \quad \text{Equation 4}$$

and $$P(\alpha) = \frac{r_\alpha^{m_\alpha} \alpha^{m_\alpha-1} e^{-r_\alpha \alpha}}{\Gamma(m_\alpha)}. \quad \text{Equation 5}$$

As well as a prior, we must be able to calculate the likelihood of the observed data. Let us suppose that during a excitation n, photons arrive at times $t_{n,1}, t_{n,2}, \ldots, t_{n,K_n}$, and at no other times. Then we have the likelihood on the data $D_n$ from excitation n given by $$P(D_n | A, \alpha) = \left( \prod_{k=1}^{K_n} (A e^{-\alpha t_{n,k}}) \right) P(\text{no other photons} | A, \alpha), \quad \text{Equation 6}$$

since in a Poisson process all events occur independently of each other. In a Poisson process of constant rate $\lambda$, the probability of no photons occurring in the interval from $t_1$, to $t_2$ is $e^{-\lambda(t_2-t_1)}$. Where the rate is not constant, this probability is $$P(D_n | A, \alpha) = \left( \prod_{k=1}^{K_n} (A e^{-\alpha t_{n,k}}) \right) e^{-\int_0^\infty \lambda(t) dt} \quad \text{Equation 7}$$

$$= A^{K_n} e^{-\alpha \sum_{k=1}^{K_n} t_{n,k} - \int_0^\infty A e^{-\alpha t} dt}$$

$$= A^{K_n} e^{-\alpha \sum_{k=1}^{K_n} t_{n,k} - \frac{A}{\alpha}}$$

We therefore have $$e^{-\int_{t_1}^{t_2} \lambda(t) dt}.$$

and combining all the data from N excitations together (independent from excitation to excitation), we have $$P(D | A, \alpha) = A^K e^{-\alpha \sum_{n=1}^N \sum_{k=1}^{K_n} t_{n,k} - \frac{NA}{\alpha}} \text{ where } K = \sum_{n=1}^N K_n.$$

Now, applying Bayes' theorem to determine the posterior, we find that $$\text{Equation 8}$$

$$P(A, \alpha | D) = \frac{P(A, \alpha) P(D | A, \alpha)}{\int P(A, \alpha) P(D | A, \alpha) dA d\alpha}$$

$$\propto \frac{r_A^{m_A} A^{m_A-1} e^{-r_A A}}{\Gamma(m_A)} \frac{r_\alpha^{m_\alpha} \alpha^{m_\alpha-1} e^{-r_\alpha \alpha}}{\Gamma(m_\alpha)} A^K e^{-\alpha(\sum_{n=1}^N \sum_{k=1}^{K_n} t_{n,k}) - \frac{NA}{\alpha}}$$

$$\propto A^{m_A-1} e^{-r_A A} \alpha^{m_\alpha-1} e^{-r_\alpha \alpha} A^K e^{-\alpha(\sum_{n=1}^N \sum_{k=1}^{K_n} t_{n,k}) - \frac{NA}{\alpha}}$$

$$= A^{K+m_A-1} \alpha^{m_\alpha-1} e^{-A(r_A+\frac{N}{\alpha})} e^{-\alpha(r_\alpha+\sum_{n=1}^N \sum_{k=1}^{K_n} t_{n,k})}$$

which gives the joint posterior distribution and hence $$\text{Equation 9}$$

$$P(\alpha | D) = \int P(A, \alpha | D) dA$$

$$\propto \int A^{K+m_A-1} \alpha^{m_\alpha-1} e^{-A(r_A+\frac{N}{\alpha})} e^{-\alpha(r_\alpha+\sum_{n=1}^N \sum_{k=1}^{K_n} t_{n,k})} dA$$

$$= \alpha^{m_\alpha-1} e^{-\alpha(r_\alpha+\sum_{n=1}^N \sum_{k=1}^{K_n} t_{n,k})} \int A^{K+m_A-1} e^{-A(r_A+\frac{N}{\alpha})} dA$$

$$= \frac{\alpha^{m_\alpha-1} e^{-\alpha(r_\alpha+\sum_{n=1}^N \sum_{k=1}^{K_n} t_{n,k})} \Gamma(K+m_A)}{\left(r_A+\frac{N}{\alpha}\right)^{K+m_A}}$$

giving the marginal distribution of a (the reciprocal of the fluorophore lifetime), while $$P(A | \alpha, D) = \frac{\left(r_A+\frac{N}{\alpha}\right)^{K+m_A}}{\Gamma(K+m_A)} A^{K+m_A-1} e^{-A(r_A+\frac{N}{\alpha})}. \quad \text{Equation 10}$$

gives the conditional distribution of initial intensity A.

With the theoretical background above, and with reference to the flowchart of FIG. 3, an algorithm suitable for software implementation will be described. The algorithm will be denoted A1. As previous discussed, although the lifetime 1/α and the initial intensity A of the fluorophore is unknown, the user normally has some vague knowledge of the possible range of these values, that can be used to generate the prior distribution needed for the Bayesian inference.

Algorithm A1:

500: In a first initialising step 500, which is included in step 300 of the flowchart of FIG. 3, the user enters functions, values or distributions describing α and A. If possible, the program may plot the result, and the user acknowledge the outcome.

505: In a measuring step 505, which corresponds to the steps 305-320, datasets of arrival times are collected $D_n$.

510: The Bayesian inference analysis, step 510 (corresponding to 325) comprises the substeps (510: 1-5) of:

510: 1 Set grid of A, α (or log A, log α).

510: 2 Calculate $$P(A, \alpha | D) = A^{K+m_A-1} \alpha^{m_\alpha-1} e^{-A(r_A+\frac{N}{\alpha})} e^{-\alpha(r_\alpha+\sum_{n=1}^N \sum_{k=1}^{K_n} t_{n,k})} \quad (\text{eq. 8})$$

for each combination of values of A and α

510: 3 Normalize the joint distribution P(A,α|D) by:
  multiplying each grid point value of P(A,α|D) by the product measure appropriate to that point,
  summing over all axes, dividing the original distribution by the result of the summation.

510: 4 Marginalize P(A,α|D) to get P(α|D) and P(A|D) (eq. 9,10) by, for each margin:
  multiplying each grid point value of P(A,α|D) by the product measure appropriate to that point,
  summing over all axes except the axis whose margin is wanted,
  dividing each grid point value of the resulting distribution by the marginal measure appropriate to that point 520: In an outputting step 520 (corresponding to 330) the resulting distributions are presented to the user as graphs, for example. Other measures can be calculated from the distribution for example the marginal means with the $5^{th}$ and $95^{th}$ centiles, an often quoted measure of the lifetime of a fluorophore.

The computational steps above usually actually need to be done by working in log P or −log P rather than in P, in order to avoid underflow and overflow. The skilled in the art will appreciate that in the calculating steps a number of obvious computational savings may be made, such as avoiding recalculating parts not changing during the summations.

The normalising step 510: 3 may preferably be performed in the following manner:

The grid of values of A are $x_h = (x_1, x_2, \ldots, x_H)$ and those of $\alpha$ are $y_j = (y_1, y_2, \ldots, y_J)$. Associate a measure with each $x_h$ and $$y_j : m(x_h) = \frac{x_{h+1} + x_h}{2} - \frac{x_h + x_{h-1}}{2} \text{ and } m(y_j) = \frac{y_{j+1} + y_j}{2} - \frac{y_j + y_{j-1}}{2} \text{ and } m(x_h, y_j) = m(x_h)m(y_j)$$

The normalised joint distribution will be given by $$P(A = x_h, \alpha = y_j \mid D) := \frac{P(A = x_h, \alpha = y_j \mid D)}{\sum_h \sum_j P(A = x_h, \alpha = y_j \mid D) m(x_h, y_j)}$$

where all the symbols indicate the values stored at the grid points and the assignment symbol := indicates new values to be stored in place of the old (which were only correct up to a constant of proportionality).

The marginalising step 510: 4 may preferably be performed by calculating:

$$P(A = x_h \mid D) := \frac{\sum_j P(A = x_h, \alpha = y_j \mid D) m(x_h, y_j)}{m(x_h)} \text{ and}$$

$$P(\alpha = y_j \mid D) := \frac{\sum_j P(A = x_h, \alpha = y_j \mid D) m(x_h, y_j)}{m(y_j)}$$

The optional calculation of marginal means with the 5$^{th}$ and 95$^{th}$ centiles in the outputting step 520 may preferably be performed by calculating the cumulative density functions;

$$P(A \leq x_h) = \sum_{h'=1}^{h} P(A = x_{h'}) m(x_{h'}) \text{ and find greatest } h \text{ such that } P(A \leq x_h) \leq 0.05 \text{ and } P(A \geq x_h) =$$

$$\sum_{h'=1}^{h} P(A = x_{h'}) m(x_{h'}) \text{ and find least } h \text{ such that } P(A \geq x_h) \leq 0.05$$

Single Fluorophore, with Photon-Induced, Initial, and Final Deadtimes and Unknown Lifetime

One of the major advantages with Bayesian inference is the possibility of introducing parameters describing e.g. equipment performance and artifacts in the analysis. The result will be the true distributions taking these parameters into account, rather than compensating a result with heuristic factors reflecting the artifacts, as in prior art.

Adopting the same notation as before, suppose that the detector is dead for a duration $\delta$ after each photon is received, for a duration $\tau$ after the excitation, and at all times longer than $\upsilon$ after excitation. Again, we must calculate the likelihood of the observed data. Let us suppose that during a excitation n, photons arrive at times $t_{n,1}, t_{n,2}, \ldots, t_{n,K_n}$, and at no other times. As before we have the likelihood on the data $D_n$ from excitation n given by $$P(D_n \mid A, \alpha) = \left( \prod_{k=1}^{K_n} (A e^{-\alpha t_{n,k}}) \right) P(\text{no other photons} \mid A, \alpha),$$

since in a Poisson process all events occur independently of each other. The difference between this expression and the corresponding one is in the meaning of the phrase "no other photons"; in the preceding section it meant no other photons ever, while now it just means no other photons in the time that the detector is live.

As before, this probability is $$e^{-\int_T \lambda(t) dt},$$

where T now denotes the set of times at which the detector is live. We therefore have $$P(\text{no other photons} \mid A, \alpha) =$$

$$e^{-\left( \int_\tau^{t_{n,1}} \lambda(t) dt + \sum_{k=1}^{K_n-1} \int_{t_{n,k}}^{t_{n,k+1}} \lambda(t) dt + \int_{t_{n,K_n}}^{\upsilon} \lambda(t) dt \right)} \approx e^{-\left( \int_\tau^\upsilon \lambda(t) dt - \sum_{k=1}^{K_n} \int_{t_{n,k}}^{t_{n,k}+\delta} \lambda(t) dt \right)}$$

where the last line follows if we make the assumption that none of the deadtimes overlap with the period following $\upsilon$. Thus $$P(\text{no other photons} \mid A, \alpha) \approx e^{-\left( \int_\tau^\upsilon \lambda(t) dt - \sum_{k=1}^{K_n} \int_{t_{n,k}}^{t_{n,k}+\delta} \lambda(t) dt \right)}$$

$$= e^{-\left( \int_\tau^\upsilon A e^{-\alpha t} dt - \sum_{k=1}^{K_n} \int_{t_{n,k}}^{t_{n,k}+\delta} A e^{-\alpha t} dt \right)}$$

$$= e^{\frac{A}{\alpha} \left( [e^{-\alpha t}]_\tau^\upsilon - \sum_{k=1}^{K_n} [e^{-\alpha t}]_{t_{n,k}}^{t_{n,k}+\delta} \right)}$$

$$= e^{-\frac{A}{\alpha} \left( (e^{-\alpha \tau} - e^{-\alpha \upsilon}) - \sum_{k=1}^{K_n} \left( e^{-\alpha t_{n,k}} - e^{-\alpha(t_{n,k}+\delta)} \right) \right)}$$

$$= e^{-\frac{A}{\alpha} \left( (e^{-\alpha \tau} - e^{-\alpha \upsilon}) - \sum_{k=1}^{K_n} \left( e^{-\alpha t_{n,k}} (1 - e^{-\alpha \delta}) \right) \right)}$$

$$= e^{-\frac{A}{\alpha} \left( (e^{-\alpha \tau} - e^{-\alpha \upsilon}) - (1 - e^{-\alpha \delta}) \sum_{k=1}^{K_n} e^{-\alpha t_{n,k}} \right)}$$

so combining all the data from N excitations together (independent from excitation to excitation), we have $$P(D \mid A, \alpha) = \prod_{n=1}^{N} \left( \left( \prod_{k=1}^{K_n} (A e^{-\alpha t_{n,k}}) \right) e^{-\frac{A}{\alpha} \left( (e^{-\alpha \tau} - e^{-\alpha \upsilon}) - (1 - e^{-\alpha \delta}) \sum_{k=1}^{K_n} e^{-\alpha t_{n,k}} \right)} \right)$$

$$= A^K e^{-\alpha \left( \sum_{n=1}^{N} \sum_{k=1}^{K_n} t_{n,k} \right) - \frac{A}{\alpha} \left( N(e^{-\alpha \tau} - e^{-\alpha \upsilon}) - (1 - e^{-\alpha \delta}) \sum_{n=1}^{N} \sum_{k=1}^{K_n} e^{-\alpha t_{n,k}} \right)}.$$

Now, applying Bayes' theorem to determine the posterior, we find that $$P(A, \alpha \mid D) = \frac{P(A, \alpha) P(D \mid A, \alpha)}{\int P(A, \alpha) P(D \mid A, \alpha) dA d\alpha} \propto \qquad \text{Equation 11}$$

$$\frac{r_A^{m_A} A^{m_A-1} e^{-r_A A}}{\Gamma(m_A)} \frac{r_\alpha^{m_\alpha} \alpha^{m_\alpha-1} e^{-r_\alpha \alpha}}{\Gamma(m_\alpha)} A^K$$

$$e^{-\alpha \left( \sum_{n=1}^{N} \sum_{k=1}^{K_n} t_{n,k} \right) - \frac{A}{\alpha} \left( N(e^{-\alpha \tau} - e^{-\alpha \upsilon}) - (1 - e^{-\alpha \delta}) \sum_{n=1}^{N} \sum_{k=1}^{K_n} e^{-\alpha t_{n,k}} \right)}$$

$$\propto A^{m_A-1} e^{-r_A A} \alpha^{m_\alpha-1} e^{-r_\alpha \alpha} A^K$$

$$e^{-\alpha \left( \sum_{n=1}^{N} \sum_{k=1}^{K_n} t_{n,k} \right) - \frac{A}{\alpha} \left( N(e^{-\alpha \tau} - e^{-\alpha \upsilon}) - (1 - e^{-\alpha \delta}) \sum_{n=1}^{N} \sum_{k=1}^{K_n} e^{-\alpha t_{n,k}} \right)}$$

$$= A^{K+m_A-1} \alpha^{m_\alpha-1}$$

$$e^{-A \left( r_A + \frac{1}{\alpha} \left( N(e^{-\alpha \tau} - e^{-\alpha \upsilon}) - (1 - e^{-\alpha \delta}) \sum_{n=1}^{N} \sum_{k=1}^{K_n} e^{-\alpha t_{n,k}} \right) \right)}$$

$$e^{-\alpha \left( r_\alpha + \sum_{n=1}^{N} \sum_{k=1}^{K_n} t_{n,k} \right)}$$

and hence $$P(\alpha \mid D) = \int P(A, \alpha \mid D) dA$$

$$\propto \int A^{K+m_A-1} \alpha^{m_\alpha-1} e^{-A\left(r_A + \frac{1}{\alpha}\left(N(e^{-\alpha\tau}-e^{-\alpha\nu})-(1-e^{-\alpha\delta})\sum_{n=1}^{N}\sum_{k=1}^{K_n} e^{-\alpha t_{n,k}}\right)\right)} e^{-\alpha\left(r_\alpha+\sum_{n=1}^{N}\sum_{k=1}^{K_n} t_{n,k}\right)} dA$$

$$= \alpha^{m_\alpha-1} e^{-\alpha\left(r_\alpha+\sum_{n=1}^{N}\sum_{k=1}^{K_n} t_{n,k}\right)} \int A^{K+m_A-1} e^{-A\left(r_A + \frac{1}{\alpha}\left(N(e^{-\alpha\tau}-e^{-\alpha\nu})-(1-e^{-\alpha\delta})\sum_{n=1}^{N}\sum_{k=1}^{K_n} e^{-\alpha t_{n,k}}\right)\right)} dA$$

$$= \frac{\alpha^{m_\alpha-1} e^{-\alpha\left(r_\alpha+\sum_{n=1}^{N}\sum_{k=1}^{K_n} t_{n,k}\right)} \Gamma(K+m_A)}{\left(r_A + \frac{1}{\alpha}\left(N(e^{-\alpha\tau}-e^{-\alpha\nu})-(1-e^{-\alpha\delta})\sum_{n=1}^{N}\sum_{k=1}^{K_n} e^{-\alpha t_{n,k}}\right)\right)^{K+m_A}}$$

Equation 12 while $$P(A \mid \alpha, D) = \frac{q^{K+m_A}}{\Gamma(K+m_A)} A^{K+m_A-1} e^{-Aq}$$

Equation 13 where $$q = r_A + \frac{1}{\alpha}\left(N(e^{-\alpha\tau} - e^{-\alpha\nu}) - (1-e^{-\alpha\delta})\sum_{n=1}^{N}\sum_{k=1}^{K_n} e^{-\alpha t_{n,k}}\right)$$

so that again the conditional posterior distribution for A given $\alpha$ is a Gamma distribution.

With a slight modification algorithm A1 can still be used:
In step 510: 2 $P(A,\alpha|D)$ will instead of equation 8 be given by equation 11 taking into account the various deadtimes:
520: Calculate $$P(A, \alpha \mid D) \propto A^{K+m_A-1} \alpha^{m_\alpha-1}$$
$$e^{-A\left(r_A+\frac{1}{\alpha}\left(N(e^{-\alpha\tau}-e^{-\alpha\nu})-(1-e^{-\alpha\delta})\sum_{n=1}^{N}\sum_{k=1}^{K_n} e^{-\alpha t_{n,k}}\right)\right)} e^{-\alpha\left(r_\alpha+\sum_{n=1}^{N}\sum_{k=1}^{K_n} t_{n,k}\right)}$$

Algorithm A2, Multiple Fluorophores, Unknown Fluorophore Lifetimes, with Deadtimes.

Now we repeat the analysis, introducing the remaining complication that there are several fluorophores, with parameters given by $A_i$, $\alpha_i$ for $i=1, \ldots, I$. The deadtimes are independent of which fluorophores the photon came from.

We then have $$P(D_n \mid A, \alpha) = \left(\prod_{k=1}^{K_n}\left(\prod_{i=1}^{I} A_i e^{-\alpha_i t_{n,k}}\right)\right) P(\text{no other photons} \mid A, \alpha),$$

where A denotes the vector of the $A_i$s, and $\alpha$ denotes the vector of $\alpha_i$s. As before, we have $P(\text{no other photons} \mid A, \alpha) =$ $$e^{-\left(\int_r^{t_{n,1}} \lambda(t)dt + \sum_{k=1}^{K_n-1}\int_{t_{n,k}}^{t_{n,k+1}}\lambda(t)dt + \int_{t_{n,K_n}}^{\nu}\lambda(t)dt\right)} \approx e^{-\left(\int_r^{\nu}\lambda(t)dt - \sum_{k=1}^{K_n}\int_{t_{n,k}}^{t_{n,k}+\delta}\lambda(t)dt\right)}$$

where the last line follows if we make the assumption that none of the deadtimes overlap with the period following $\upsilon$. Thus $$P(\text{no other photons} \mid A, \alpha) \approx e^{-\left(\int_r^{\nu}\lambda(t)dt - \sum_{k=1}^{K_n}\int_{t_{n,k}}^{t_{n,k}+\delta}\lambda(t)dt\right)}$$

$$= e^{-\left(\int_r^{\nu}\sum_{i=1}^{I} A_i e^{-\alpha_i t} dt - \sum_{k=1}^{K_n}\int_{t_{n,k}}^{t_{n,k}+\delta}\sum_{i=1}^{I} A_i e^{-\alpha_i t} dt\right)}$$

$$= e^{\sum_{i=1}^{I}\frac{A_i}{\alpha_i}\left([e^{-\alpha_i t}]_\tau^\nu - \sum_{k=1}^{K_n}[e^{-\alpha_i t}]_{t_{n,k}}^{t_{n,k}+\delta}\right)}$$

$$= e^{-\sum_{i=1}^{I}\frac{A_i}{\alpha_i}\left((e^{-\alpha_i\tau}-e^{-\alpha_i\nu})-\sum_{k=1}^{K_n}\left(e^{-\alpha_i t_{n,k}}-e^{-\alpha_i(t_{n,k}+\delta)}\right)\right)}$$

$$= e^{-\sum_{i=1}^{I}\frac{A_i}{\alpha_i}\left((e^{-\alpha_i\tau}-e^{-\alpha_i\nu})-\sum_{k=1}^{K_n}\left(e^{-\alpha_i t_{n,k}}(1-e^{-\alpha_i\delta})\right)\right)}$$

$$= e^{-\sum_{i=1}^{I}\frac{A_i}{\alpha_i}\left((e^{-\alpha_i\tau}-e^{-\alpha_i\nu})-(1-e^{-\alpha_i\delta})\sum_{k=1}^{K_n} e^{-\alpha_i t_{n,k}}\right)}$$

so combining all the data from N excitations together (independent from excitation to excitation), we have $$P(D \mid A, \alpha) = \prod_{n=1}^{N}\left(\left(\prod_{k=1}^{K_n}\left(\sum_{i=1}^{I} A_i e^{-\alpha_i t_{n,k}}\right)\right) e^{-\sum_{i=1}^{I}\frac{A_i}{\alpha_i}\left((e^{-\alpha_i\tau}-e^{-\alpha_i\nu})-(1-e^{-\alpha_i\delta})\sum_{k=1}^{K_n} e^{-\alpha_i t_{n,k}}\right)}\right)$$

$$= \left(\prod_{n=1}^{N}\prod_{k=1}^{K_n}\sum_{i=1}^{I} A_i e^{-\alpha_i t_{n,k}}\right) e^{-\sum_{n=1}^{N}\sum_{i=1}^{I}\frac{A_i}{\alpha_i}\left((e^{-\alpha_i\tau}-e^{-\alpha_i\nu})-(1-e^{-\alpha_i\delta})\sum_{k=1}^{K_n} e^{-\alpha_i t_{n,k}}\right)}$$

$$= \left(\prod_{n=1}^{N}\prod_{k=1}^{K_n}\sum_{i=1}^{I} A_i e^{-\alpha_i t_{n,k}}\right) e^{-N\sum_{i=1}^{I}\frac{A_i}{\alpha_i}(e^{-\alpha_i\tau}-e^{-\alpha_i\nu})+\sum_{i=1}^{I}\left(\frac{A_i}{\alpha_i}(1-e^{-\alpha_i\delta})\sum_{n=1}^{N}\sum_{k=1}^{K_n} e^{-\alpha_i t_{n,k}}\right)}.$$

Now, applying Bayes' theorem to determine the posterior, we find that $$P(A, \alpha | D) = \frac{P(A, \alpha)P(D | A, \alpha)}{\int P(A, \alpha)P(D | A, \alpha) dA d\alpha}$$

Equation 14

$$\propto \prod_{i=1}^{I} \frac{r_{A_i}^{m_{A_i}} A_i^{m_{A_i}-1} e^{-r_{A_i} A_i}}{\Gamma(m_{A_i})} \prod_{i=1}^{I} \frac{r_{\alpha_i}^{m_{\alpha_i}} \alpha_i^{m_{\alpha_i}-1} e^{-r_{\alpha_i} \alpha_i}}{\Gamma(m_{\alpha_i})}$$

$$\left(\prod_{n=1}^{N} \prod_{k=1}^{K_n} \sum_{i=1}^{I} A_i e^{-\alpha_i t_{n,k}}\right) e^{-N \sum_{i=1}^{I} \frac{A_i}{\alpha_i}(e^{-\alpha_i \tau} - e^{-\alpha_i \nu}) + \sum_{i=1}^{I} \left(\frac{A_i}{\alpha_i}(1-e^{-\alpha_i \delta})\sum_{n=1}^{N} \sum_{k=1}^{K_n} e^{-\alpha_i t_{n,k}}\right)}$$

$$\propto \left(\prod_{i=1}^{I} A_i^{m_{A_i}-1} \alpha_i^{m_{\alpha_i}-1}\right) \left(\prod_{n=1}^{N} \prod_{k=1}^{K_n} \sum_{i=1}^{I} A_i e^{-\alpha_i t_{n,k}}\right)$$

$$e^{-\sum_{i=1}^{I} r_{A_i} A_i - \sum_{i=1}^{I} r_{\alpha_i} \alpha_i - N \sum_{i=1}^{I} \frac{A_i}{\alpha_i}(e^{-\alpha_i \tau} - e^{-\alpha_i \nu}) + \sum_{i=1}^{I} \left(\frac{A_i}{\alpha_i}(1-e^{-\alpha_i \delta})\sum_{n=1}^{N} \sum_{k=1}^{K_n} e^{-\alpha_i t_{n,k}}\right)}$$

$$= \left(\prod_{i=1}^{I} A_i^{m_{A_i}-1} \alpha_i^{m_{\alpha_i}-1}\right) \left(\prod_{n=1}^{N} \prod_{k=1}^{K_n} \sum_{i=1}^{I} A_i e^{-\alpha_i t_{n,k}}\right) e^{-\sum_{i=1}^{I} \left(r_{A_i} A_i + r_{\alpha_i} \alpha_i + \frac{A_i}{\alpha_i}(N(e^{-\alpha_i \tau} - e^{-\alpha_i \nu}) - (1-e^{-\alpha_i \delta})\sum_{n=1}^{N} \sum_{k=1}^{K_n} e^{-\alpha_i t_{n,k}})\right)}$$

We now use algorithm A2, which though it appears similar to A1 differs in step 520 where $P(A,\alpha|D)$ will be given, instead of by equation 8, by equation 14 taking into account the various deadtimes and the possibility of a plurality of unknown fluorophore lifetimes and/or intensities.

510: 2 Calculate, for each point on the multidimensional grid, $$P(A, \alpha | D) = \left(\prod_{i=1}^{I} A_i^{m_{A_i}-1} \alpha_i^{m_{\alpha_i}-1}\right) \left(\prod_{n=1}^{N} \prod_{k=1}^{K_n} \sum_{i=1}^{I} A_i e^{-\alpha_i t_{n,k}}\right)$$

$$e^{-\sum_{i=1}^{I} \left(r_{A_i} A_i + r_{\alpha_i} \alpha_i + \frac{A_i}{\alpha_i}(N(e^{-\alpha_i \tau} - e^{-\alpha_i \nu}) - (1-e^{-\alpha_i \delta})\sum_{n=1}^{N} \sum_{k=1}^{K_n} e^{-\alpha_i t_{n,k}})\right)}$$

As can be understood both from the appearance of equation 14 and, more importantly, from the fact that the grid is now multidimensional, this alternative of algorithm A1 will often be computational heavy and time-consuming.

Algorithm A3, Multiple Fluorophores with Known Lifetimes

A third embodiment of the inventive method of the present invention refers to measurement cases in which the lifetimes of the fluorophores in the sample are known. This can be the case for example when complex organic molecules are "tagged" with known fluorophores. The wanted measure may then be for example the quantities of the fluorophores, reflected in the initial intensities $A_i$, or the ratios between the quantities of the different fluorophores, reflected in the ratios of the initial intensities $A_j$.

Equation 14 above is simplified in the case of known lifetimes:

$$P(A | D) \propto \left(\prod_{i=1}^{I} A_i^{m_{A_i}-1}\right) \left(\prod_{n=1}^{N} \prod_{k=1}^{K_n} \sum_{i=1}^{I} A_i e^{-\alpha_i t_{n,k}}\right)$$

$$e^{-\sum_{i=1}^{I} \left(r_{A_i} A_i + \frac{A_i}{\alpha_i}(N(e^{-\alpha_i \tau} - e^{-\alpha_i \nu}) - (1-e^{-\alpha_i \delta})\sum_{n=1}^{N} \sum_{k=1}^{K_n} e^{-\alpha_i t_{n,k}})\right)}$$

but this is not sufficient to get a simple fast implementation, because of the number of terms in the second factor. By, in addition, inferring which fluorophore each photon came from it will be shown that the computation can be simplified, and hence the time needed for the Bayesian inference analysis is significantly shorter. Surprisingly, we gain here by introducing a large number of extra variables—in fact we introduce I new variables per photon received. For each photon $\phi_{n,k}$ received we introduce the I variables $s_{n,k,i}$, which is defined to be 1 if $\phi_{n,k}$ is emitted by fluorophore i and is 0 otherwise. The s variable tells which fluorophore a photon originates from. Let S denote the Cartesian product of all these new variables.

We can then recomplicate the above equation as follows:

$$P(A | D) = \int P(A, S | D) dS = \frac{\int P(A)P(D | A)P(S | D, A) dS}{P(D)}$$

$$\propto \int \left(\prod_{i=1}^{I} A_i^{m_{A_i}-1}\right) \left(\prod_{n=1}^{N} \prod_{k=1}^{K_n} \sum_{i=1}^{I} A_i e^{-\alpha_i t_{n,k}}\right) e^{-\sum_{i=1}^{I} \left(r_{A_i} A_i + \frac{A_i}{\alpha_i}(N(e^{-\alpha_i \tau} - e^{-\alpha_i \nu}) - (1-e^{-\alpha_i \delta})\sum_{n=1}^{N} \sum_{k=1}^{K_n} e^{-\alpha_i t_{n,k}})\right)} P(S | D, A) dS$$

Now, $$P(S | D, A) = \prod_{n=1}^{N} \prod_{k=1}^{K_n} P(s_{n,k} | D, A) = \prod_{n=1}^{N} \prod_{k=1}^{K_n} P(s_{n,k} | \text{photon referred to by } s_{n,k} \text{ is at } t_{n,k}, A)$$

$$= \prod_{n=1}^{N} \prod_{k=1}^{K_n} \frac{P(\text{there is a photon from fluor } i \text{ at } t_{n,k} | A)}{\sum_{i=1}^{I} P(\text{there is a photon from fluor } i \text{ at } t_{n,k} | A)} = \prod_{n=1}^{N} \prod_{k=1}^{K_n} \frac{\sum_{i=1}^{I} s_{n,k,i} A_i e^{-\alpha_i t_{n,k}}}{\sum_{i=1}^{I} A_i e^{-\alpha_i t_{n,k}}}$$

therefore $$P(A\mid D) \propto \int \left(\prod_{i=1}^{I} A_i^{m_{A_i}-1}\right)\left(\prod_{n=1}^{N}\prod_{k=1}^{K_n}\left(\frac{\sum_{i=1}^{I} s_{n,k,i} A_i e^{-\alpha_i t_{n,k}}}{\sum_{i=1}^{I} A_i e^{-\alpha_i t_{n,k}}}\sum_{i=1}^{I} A_i e^{-\alpha_i t_{n,k}}\right)\right) e^{-\sum_{i=1}^{I}\left(r_{A_i} A_i + \frac{A_i}{\alpha_i}\left(N(e^{-\alpha_i \tau}-e^{-\alpha_i \nu})-(1-e^{-\alpha_i \delta})\sum_{n=1}^{N}\sum_{k=1}^{K_n} e^{-\alpha_i t_{n,k}}\right)\right)} dS$$

$$= \int \left(\prod_{i=1}^{I} A_i^{m_{A_i}-1}\right)\left(\prod_{n=1}^{N}\prod_{k=1}^{K_n}\sum_{i=1}^{I} s_{n,k,i} A_i e^{-\alpha_i t_{n,k}}\right) e^{-\sum_{i=1}^{I}\left(r_{A_i} A_i + \frac{A_i}{\alpha_i}\left(N(e^{-\alpha_i \tau}-e^{-\alpha_i \nu})-(1-e^{-\alpha_i \delta})\sum_{n=1}^{N}\sum_{k=1}^{K_n} e^{-\alpha_i t_{n,k}}\right)\right)} dS$$

By simply removing the integration throughout the above argument, we can also arrive at $$P(A, S \mid D) \propto \left(\prod_{i=1}^{I} A_i^{m_{A_i}-1}\right)\left(\prod_{n=1}^{N}\prod_{k=1}^{K_n}\sum_{i=1}^{I} s_{n,k,i} A_i e^{-\alpha_i t_{n,k}}\right)$$

$$e^{-\sum_{i=1}^{I}\left(r_{A_i} A_i + \frac{A_i}{\alpha_i}\left(N(e^{-\alpha_i \tau}-e^{-\alpha_i \nu})-(1-e^{-\alpha_i \delta})\sum_{n=1}^{N}\sum_{k=1}^{K_n} e^{-\alpha_i t_{n,k}}\right)\right)}$$

Equation 15 which is the starting point for algorithm A3.

We now plan to take random samples from the joint distribution of A and S. In order to do so we will use Markov Chain Monte Carlo techniques. In particular, given a random sample $(A_j, S_j)$ we will, if j is even, set $S_{j+1}$ equal to $S_j$, and draw $A_{j+1}$, from $P(A|S_{j+1})$, and if j is odd, set $A_{j+1}$ equal to $A_j$ and draw $S_{j+1}$, from $P(S|A_{j+1})$.

Drawing $S_{j+1}$ from $P(S\uparrow A_{j+1})$ is easy, because this conditional distribution of S is separable over its K components $S_{n,k}$, and each of these is a simple discrete distribution:

$$P(S\mid A, D) \propto \prod_{n=1}^{N}\prod_{k=1}^{K_n}\sum_{i=1}^{I} s_{n,k,i} A_i e^{-\alpha_i t_{n,k}}$$

$$\therefore P(s_{n,k,i}=1, (\forall\, i' \neq i) s_{n,k,i'}=0 \mid A, D) = \frac{A_i e^{-\alpha_i t_{n,k}}}{\sum_{i=1}^{I} A_i e^{-\alpha_i t_{n,k}}}$$

Equation 16 and each $s_{n,k}$ may be handled independently.

Drawing $A_{j+1}$ from $P(A|S_{j+1})$ requires sampling from 1 Gamma distributions; how to do this will be exemplified in an appendix. The distributions in question are given by:

$$P(A \mid S, D) \propto \left(\prod_{i=1}^{I} A_i^{m_{A_i}-1}\right)\left(\prod_{i=1}^{I}\prod_{n=1}^{N}\prod_{k=1}^{K_n} A_i e^{-\alpha_i t_{n,k}}\right) e^{-\sum_{i=1}^{I}\left(r_{A_i} A_i + \frac{A_i}{\alpha_i}\left(N(e^{-\alpha_i \tau}-e^{-\alpha_i \nu})-(1-e^{-\alpha_i \delta})\sum_{n=1}^{N}\sum_{k=1}^{K_n} e^{-\alpha_i t_{n,k}}\right)\right)}$$

$$\therefore P(A_i \mid S, D) = A_i^{m_{A_i}-1+\sum_{n=1}^{N}\sum_{k=1}^{K_n} s_{n,k,i}} e^{-A_i\left(r_{A_i}+\frac{1}{\alpha_i}\left(N(e^{-\alpha_i \tau}-e^{-\alpha_i \nu})-(1-e^{-\alpha_i \delta})\sum_{n=1}^{N}\sum_{k=1}^{K_n} e^{-\alpha_i t_{n,k}}\right)\right)}$$

Equation 17

Having got our sequence of random samples $(A_1, S_1), (A_2, S_2), \ldots$ we convert it into a sequence of samples of A by discarding the values of S.

With the theoretical background above, and with reference to the flowchart of FIG. 3, an algorithm suitable for software implementation will be described. The algorithm will be denoted A3.

Algorithm A3:

600: In a first initialising step 600, which is included in step 300 of the flowchart of FIG. 3, the user enters functions, values or distributions describing a and A.

600: 1 a) If based on information from previous experiments:

600: 1.1 i) and if posterior of previous experiments are of Gamma form (eq. 3):
copy m and r from the posterior of the previous experiment 600: 1.2 ii) if other distribution form, e.g. $f(A_i)$:
plot $f(A_i)$ and adjust $m_{A_i}, r_{A_i}$ until Gamma functions mimic $f(A_i)$ or
consider information loss $$I_{m,r} = \int f(A) \log \frac{f(A)}{\Gamma_{m,r}(A)} dA$$

and adjust m and r
for minimum $I_{m,r}$ using some minimisation routine.

600: 2 b) If information is vague knowledge of fluorophore;
for each fluorophore pick $m_{A_i}, r_{A_i}$, so that distribution fits "mental image":

600: 2.1 i) for each $A_i$ do

600: 2.1.1 a) pick $m_{A_i} > 0$ (that the larger the value the narrower the prior)

600: 2.1.2 b) pick mean μ of prior (e.g. $10^8$ meaning 1 photon per 10 ns)

600: 2.1.3 c) set $r_{A_i} = m_{A_i}/\mu$

600: 2.1.4 d) plot prior on screen (linear or log scale)

600: 2.1.5 e) Does the plot fit the mental image desired?
Yes—new $A_i$ (goto i), No—repeat (a) to (e) as necessary 605: In a measuring step 605, which corresponds to the steps 305-320, datasets of arrival times are collected $D_n$.

610: The Bayesian inference analysis, step 610 (corresponding to 325) comprises the substeps (610: 1-4) of:
610: 1 Initialize:
610: 1.1 set number of samples required
610: 1.2 select a starting value for each 4, options:
  i) select random sample from prior on $A_i$
  ii) select mean from prior on $A_i$
  iii) select mode from prior on $A_i$
  iv) user input data
610: 2 Update $S(s_{n,k}$ representing the source of each photon)
610: 2.1 For each $n(1, 2, \ldots, K_n)$
610: 2.1.1 For each $k(1, 2, \ldots, K_n)$
610: 2.1.1.1 Update $s_{n,k}$:
  select a random sample from the discrete distribution (eq. 17):

$$P(s_{n,k,i} = 1, (\forall i' \neq i) s_{n,k,i'} = 0 \mid A, D) = \frac{A_i e^{-\alpha_i t_{n,k}}}{\sum_{i=1}^{I} A_i e^{-\alpha_i t_{n,k}}}$$

610: 2.1.2 Next k
610: 2.2 Next n
610: 3 Update A
610: 3.1 For each $i(1, 2, \ldots, I)$
610: 3.1.1 Update $A_i$:
610: 3.1.1.1 Calculate $$m = m_{A_i} + \sum_{n=1}^{N} \sum_{k=1}^{K_n} s_{n,k,i}$$

610: 3.1.1.2 Calculate $$r_i = r_{A_i} + \frac{1}{\alpha_i}\left(N(e^{-\alpha_i \tau} - e^{-\alpha_i \nu}) - (1 - e^{-\alpha_i \delta})\sum_{n=1}^{N}\sum_{k=1}^{K_n} e^{-\alpha_i t_{n,k}}\right)$$

610: 3.1.1.3 Set new value of $A_i$ to be a random sample from the Gamma distribution with parameters m, $r_i$ (see Appendix)
610: 3.1 Next i
610: 4 Add value of A to list of samples of A
610: 5 Enough samples? Yes—goto 620, No—repeat 610: 2-5
620: In an outputting step 620 (corresponding to 330) the resulting list of samples is presented to the user. Optionally histograms (corresponding to the marginal distributions of previous algorithms) can be presented. Other measures can be calculated from the histograms for example the marginal means with the $5^{th}$ and $95^{th}$ centiles.

Alternatively it is equally feasible to start with the source variables S. The algorithm would be slightly modified, the important modifications are:
610: 1 Initialize:
  select some value at random for each $s'_{n,k}$ defined by $$s'_{n,k} \equiv \sum_{i=1}^{I} i s_{n,k,i}$$

from the set $\{1, 2, \ldots, I\}$ and
610: 2 Update A
610: 3 Update S

Note that the procedure, in step 610: 3, to draw a random sample from the Gamma distribution with parameters $m, r_i$ can be done in various ways. A suitable method will be described in the Appendix.

Figure 5:
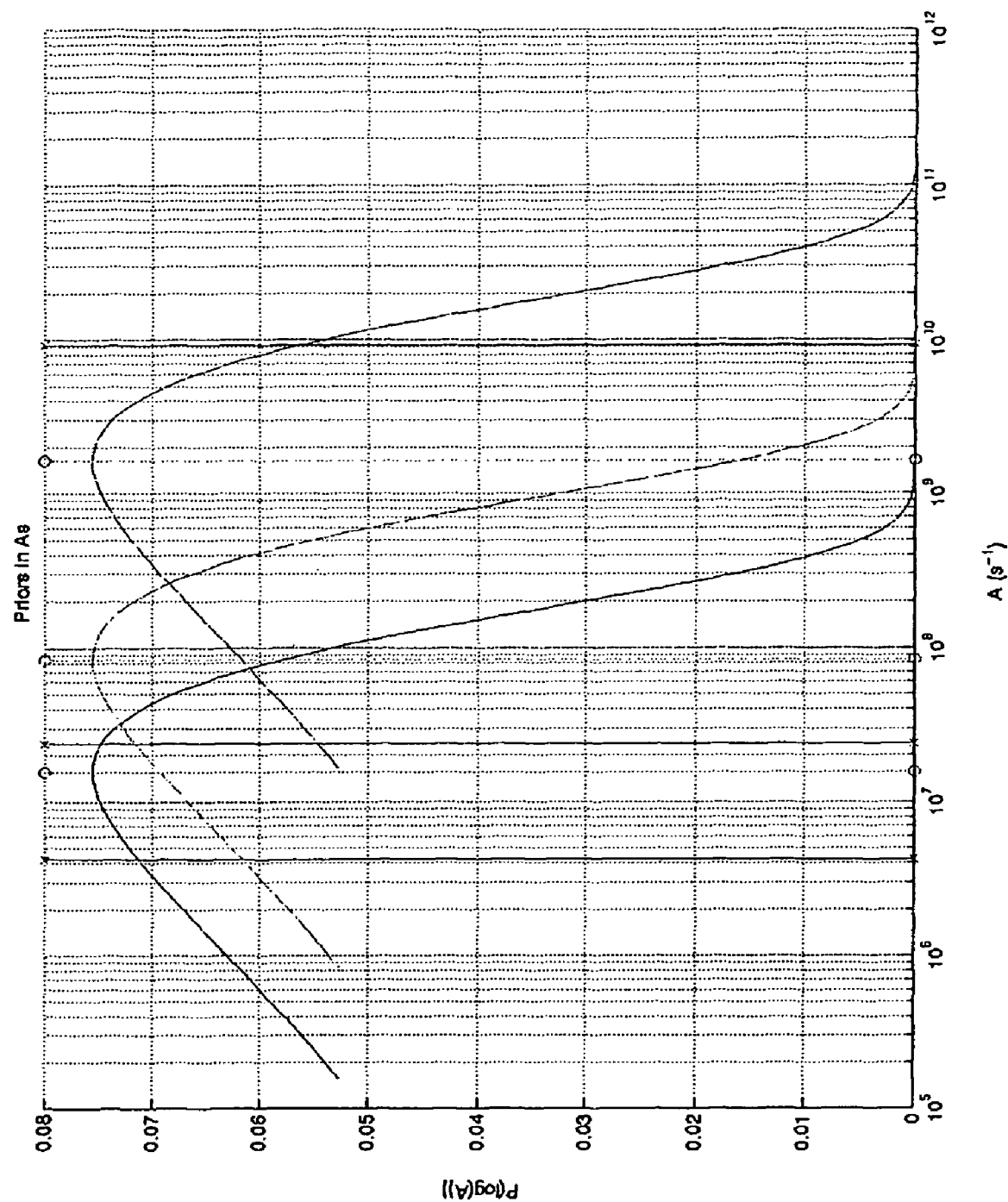
FIG. 5 is a graph showing an example of three prior distributions entered by a user.
Figure 6:
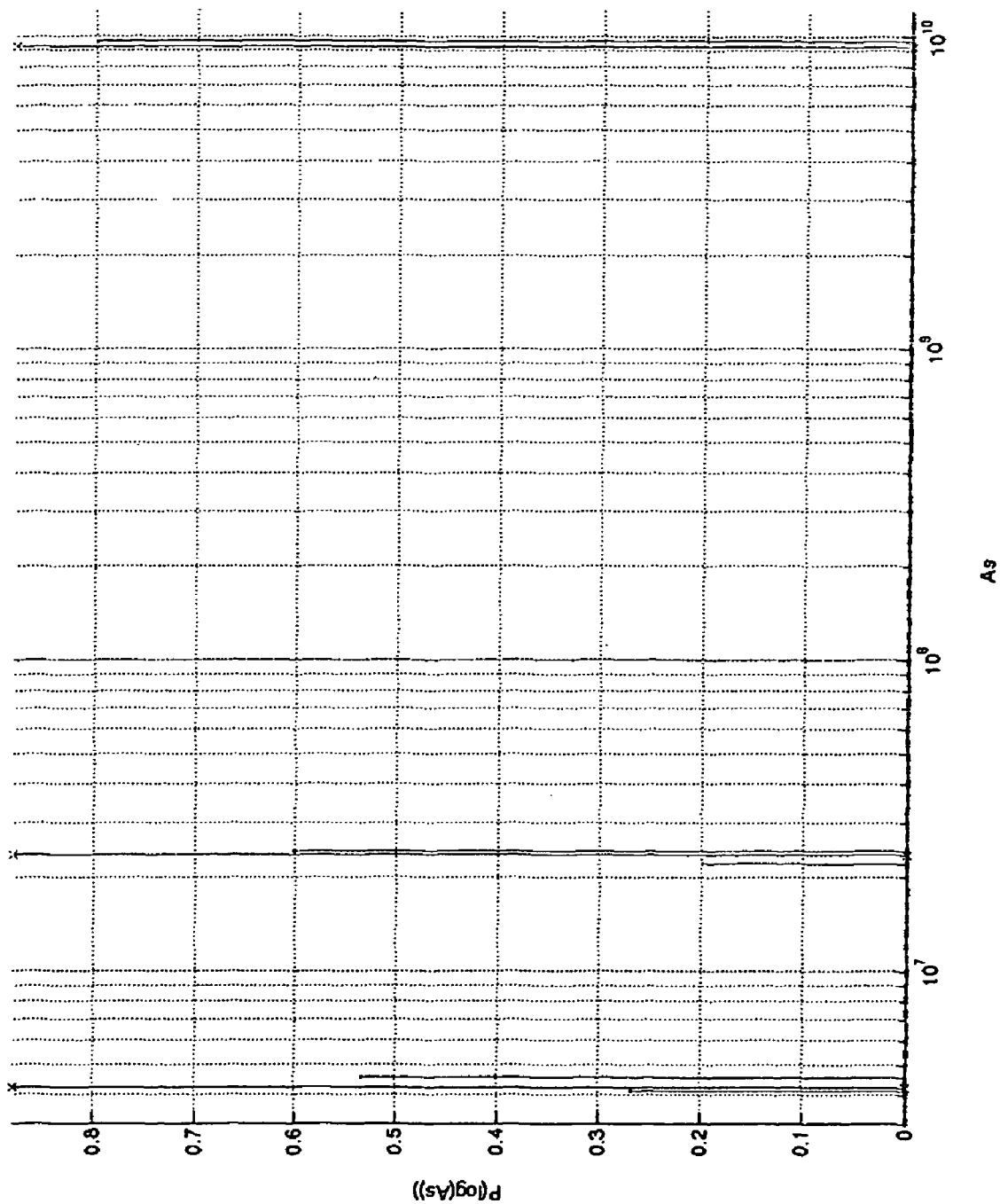
FIG. 6 is a graph showing an exemplary output from algorithms A3-A8.

FIG. 5 illustrates three prior distributions entered by a user in substep 610:1. In FIG. 6 is a typical output from step 620 shown. FIG. 6 shows histograms for three different fluorophores. The x-marked lines indicate true values.

As apparent to the skilled in the art the above algorithm can be converted to software code in many different ways and care should be taken to achieve computationally effective and efficient code, e.g. in the loops calculate only the parts that change in the loop. Such, and other simplifications, should be obvious to the skilled programmer and not considered to be a part of the invention.

Algorithms A4, A5, and A6: Multiple Fluorophores with Known Lifetimes and Binning of the Photon Times In a further embodiment of the inventive method of the present invention the previous algorithm (A3) is modified to also account for the fact that the measurement system has a finite resolution in time. The resolution of the instrument is typically given by the sampling rate of the photon timing unit 150, which could be of the order of 2G samples/s, giving a resolution of 0.5 ns. The finite resolution has the effect that it is not possible to separate in time photons arriving less than the time resolution apart; they are "binned" together. Instead of a set of arrival times, the data really consist of a fixed set of bin positions and for each excitation the number of photons arriving in each bin. This binning in time of the arrival times of the photons can be advantageously utilized in the Bayesian inference analysis; indeed algorithm A4 may in some ways be more useful than A3 even when the data are not binned, as it is easy to bin the data before using an inference algorithm.

Considering the procedure of algorithm A3, and in particular the step when we resample $A_{j+1}$ from $P(A|S_{j+1})$, we note that the only dynamic information we need to do this, other than the photon arrival times, is the set of quantities $$\sum_{n=1}^{N} \sum_{k=1}^{K_n} s_{n,k,i},$$

as we can see from the resampling equation (which defines the parameters of a Gamma distribution):

$$P(A_i|S, D) = A_i^{m_{A_i} - 1 + \sum_{n=1}^{N} \sum_{k=1}^{K_n} s_{n,k,i}} \quad \text{Equation 18}$$
$$e^{-A_i\left(r_{A_i} + \frac{1}{\alpha_i}(N(e^{-\alpha_i \tau} - e^{-\alpha_i \nu}) - (1 - e^{-\alpha_i \delta})\sum_{n=1}^{N}\sum_{k=1}^{K_n} e^{-\alpha_i t_{n,k}})\right)}.$$

However, this set of quantities simply tells us how many photons are believed, by the current posterior sample, to come from each fluorophore.

Similarly, when resampling $S_{j+1}$ from $P(S|A_{j+1})$, the only dynamic information we need is the value of $A_{j+1}$, as can be seen from the resampling equation (which defines a discrete distribution):

$$P(s_{n,k,i} = 1, (\forall i' \neq i)s_{n,k,j'} = 0 \mid A, D) = \frac{A_i e^{-\alpha_i t_{n,k}}}{\sum_{i=1}^{I} A_i e^{-\alpha_i t_{n,k}}}.$$ Equation 19

Thus it doesn't matter whether we remember or forget which photon is currently believed to come from which fluorophore; simply remembering how many there are in each time bin, and how many (total) are allocated to each fluorophore, is sufficient.

Instead of keeping track of, and resampling, the S variables then, we need only remember, and resample, the number of photons in each time bin believed to come from each fluorophore.

Formally then, we define $b_{k,i}$ to be the number of photons in time bin k that came from fluorophore i, taking all the excitations together. Let $c_{n,k}$ be the total number of photons in time bin k of excitation n; then C constitutes the data. Let $d_k$ be the midtime of bin k and $w_k$ be its width; we assume that for all other t in that same bin $$e^{-max_i(\alpha_i)t}$$

differs negligibly from $$e^{-max_i(\alpha_i)d_k}$$

(and if this is not so we will use algorithm A7 below instead).

As can be seen from the resampling equation for $S_{j+1}$ therefore, the conditional distribution of $b_k$ given $A_{j+1}$ will be multinomial, with multi-way toss probabilities given by $$EMBED \frac{w_k A_i e^{-\alpha_i d_k}}{\sum_{i=1}^{I} w_k A_i e^{-\alpha_i d_k}} = \frac{A_i e^{-\alpha_i d_k}}{\sum_{i=1}^{I} A_i e^{-\alpha_i d_k}},$$

and total number of tosses $$\sum_{n=1}^{N} c_{n,k}.$$ Equation 20

For odd j we now draw a sample from a multinomial distribution with the multi-way toss probabilities defined above, while for even j we resample $A_{j+1}$ according to $$P(A_i \mid B, D) = A_i^{m_{A_i} - 1 + \sum_{k=1}^{K} b_{k,i}}$$ Equation 21
$$e^{-A_i \left(r_{A_i} + \frac{1}{\alpha_i}(N(e^{-\alpha_i \tau} - e^{-\alpha_i \nu}) - (1 - e^{-\alpha_i \delta}) \sum_{n=1}^{N} \sum_{k=1}^{K} c_{n,k} e^{-\alpha_i d_k})\right)}$$

How to draw samples from a multinomial distribution efficiently will be shown in appendix. Asymptotically it takes only as long as the square root of the total number of photons in the bin multiplied by the largest toss probability. The run time is no longer, as in algorithm A3, proportional to the number of photons received, but to the square root of that number.

With the above reasoning and derivation algorithm A3 can be modified accordingly and is described below and with references to the flowcharts of FIG. 3.

Algorithm A4:

700: In a first initialising step 700, which is included in step 300 of the flowchart of FIG. 3, the user enters functions, values or distributions describing α and A.

700: 1 a) If information from previous experiments:

700: 1.1 i) and if posterior of previous experiments are of Gamma form (eq. 3):

copy m and r from the posterior of the previous experiment

700: 1.2 ii) if other distribution form, e.g. $f(A_i)$:

plot $f(A_i)$ and adjust $m_{A_i}, r_{A_i}$ until Gamma functions mimics $f(A_i)$ or consider information loss $$I_{m,r} = \int f(A) \log \frac{f(A)}{\Gamma_{m,r}(A)} dA$$

and adjust m and r for minimum $I_{m,r}$ using some minimisation routine.

700: 2 b) If information is vague knowledge of fluorophore; for each fluorophore pick $m_{A_i}, r_{A_i}$ r so that distribution fits "mental image":

700: 2.1 i) for each $A_i$ do

700: 2.1.1 a) pick $m_{A_i} > 0$ (that the larger the value the narrower the prior)

700: 2.1.2 b) pick mean μ of prior (e.g. 1080-1 photon per 10 ns)

700: 2.1.3 c) set $r_{A_i} = m_{A_i}/\mu$

700: 2.1.4 d) plot prior on screen (linear or log scale)

700: 2.1.5 e) does the plot match the desired mental image? Yes—new $A_i$ (goto i), No—repeat (a) to (e) as necessary 705: In a measuring step 705, which corresponds to the steps 305-320, datasets of arrival times are collected $D_n$.

710: The Bayesian inference analysis, step 710 (corresponding to 325) comprises the substeps (710: 1-4) of:

710: 1 Initialize:

710: 1.1 set bin size and position (from hardware design)

710: 1.2 count photons in each time bin:

$$c_k = \sum_{n=1}^{N} c_{n,k}$$

710: 1.3 set number of samples required

710: 1.4 select starting value for each $A_i$, options:

i) select random sample from prior on $A_i$ ii) select mean from prior on $A_i$ iii) select mode from prior on $A_i$ iv) user input data 710: 2 Update B 710: 2.1 For each k(1, 2, . . . , K)

710: 2.1.1 Update $b_k$

710: 2.1.1.1 set $b_k$ to be a random sample from the multinomial distribution with $$c_k = \sum_{n=1}^{N} c_{n,k}$$

total tosses and toss probabilities $$p_i = \frac{A_i e^{-\alpha_i d_k}}{\sum_{i=1}^{I} A_i e^{-\alpha_i d_k}} \text{ (see Appendix)}$$

710: 2.2 Next k
710: 3 Update A
710: 3.1 For each i(1, 2, ..., I)
710: 3.1.1 Update $A_i$
710: 3.1.1.1 Calculate $$m = m_{A_i} + \sum_{n=1}^{N} \sum_{k=1}^{K} b_{k,i}$$

710: 3.1.1.2 Calculate $$r_i = r_{A_i} + \frac{1}{\alpha_i}\left(N(e^{-\alpha_i \tau} - e^{-\alpha_i \nu}) - (1 - e^{-\alpha_i \delta})\sum_{n=1}^{N}\sum_{k=1}^{K} c_k e^{-\alpha_i d_k}\right)$$

710: 3.1.1.3 Set new value of $A_i$ to be a random sample from the Gamma distribution with parameters m, $r_i$ (see Appendix)
710: 3.2 Next i
710: 4 Add value of A to list of samples of A
710: 5 Enough samples? Yes—goto 720, No—repeat 710: 1-5
720: In an outputting step 720 (corresponding to 330) the resulting list of samples is presented to the user. Optionally histograms (corresponding to the marginal distributions of previous algorithms) can be presented. Other measures can be calculated from the histograms for example the marginal means with the 5th and 95th centiles and/or fractions of total intensity.

Similarly to previous algorithm it is possible to reverse the order of updating A and B with slight modifications of the algorithm.

The majority of the running time of algorithm A4 is occupied in drawing random samples from multinomial distributions (substep 710: 2). Replacing those samples with their mean will result in a faster algorithm. A noticeable deterioration in accuracy of the result can be expected, although under some circumstances it may still be considered usable. The algorithm modified in this way will be referred to as A5, A further simplification is to replace the Gamma samples (substep 710: 3) with their means, which will result in an even faster but very inaccurate algorithm, which will be referred to as A6.

Algorithm A7. Multiple Fluorophore with Known Lifetimes and Binning of the Photon Times in Bins and Subbins A further embodiment of the inventive method of the present invention illustrates the power and usefulness of the method. Suppose the bins introduced in the previous algorithm are too large, i.e. the resolution of the instrument is lower than apparently needed for the specific measurement. The algorithm described below, will by introducing subbins, dividing each bin into a number of subbins, make it possible to extract information that would otherwise been obscured by the resolution of the instrument. The subbins do not necessarily have to be of equal size, for example they could be spaced logarithmically; nor is it necessary that each bin contains the same number of subbins as each other bin.

We now introduce a number of extra variables similar to the B variables, but indicating not only which fluorophore each photon comes from, but also which subbin it falls in within the bin in which it is known to fall.

Resampling of $A_{j+1}$ from $P(A|B_{j+1})$ occurs in exactly the same way as in A4. Resampling of $B_{j+1}$ from $P(B|A_{j+1})$, however, now occurs over, for each bin, a multinomial distribution with the number of options being the product of the number of fluorophores and the number of subbins, and the total number of tosses being the total number of photons in that bin, and the multi-way toss probabilities being determined by the subbin centre time and fluorophore decay time that are relevant. Finally, of course, we discard the subbin information just as we discard the B variable information.

In detail then, suppose the original time bins are centered on times $d_k$ as before, but that bin k is now divided into $L_k$ subbins with times centered on $d_{k,l}$ and of width $w_{k,j}$. Similarly, let $b_{k,i,l}$ denote the number of photons currently supposed to have come from fluorophore i and to be in subbin l of bin k. Then the multinomial distribution over which we have to resample $b_k$ has now $IL_k$ possible toss outcomes, still with Equation 22

$$\text{EMBED, } \frac{w_{k,l}A_i e^{-\alpha_i d_{k,l}} e^{\sum_{i'=1}^{I}\left(\frac{A_{i'}}{\alpha_{i'}}(1-e^{-\alpha_i \delta})\sum_{k=1}^{K} e^{-\alpha_{i'} d_{k,l}}\right)}}{\sum_{i=1}^{i}\sum_{l=1}^{L_k} w_{k,l}A_i e^{-\alpha_i d_{k,l}} e^{\sum_{i'=1}^{I}\left(\frac{A_{i'}}{\alpha_{i'}}(1-e^{-\alpha_i \delta})\sum_{k=1}^{K} e^{-\alpha_{i'} d_{k,l}}\right)}}$$

total tosses. However, calculating the toss probabilities is slightly more difficult than it was before. Working from equation 20 for P(A,S|D), we find that the probability for toss outcome (i,l) in bin k is $$\sum_{n=1}^{N} c_{n,k}$$

while when resampling $A_{j+1}$ we must work from

Equation 23

$$P(A_i | B, D) = A_i^{m_{A_i}-1+\sum_{k=1}^{K}\sum_{l=1}^{L_k} b_{k,i,j}}$$
$$e^{-A_i\left(r_{A_i}+\frac{1}{\alpha_i}(N(e^{-\alpha_i \tau}-e^{-\alpha_i \nu})-(1-e^{-\alpha_i \delta})\sum_{k=1}^{K}\sum_{l=1}^{L_k}\left(e^{-\alpha_i d_{k,l}}\sum_{i'=1}^{I} b_{k,i',l}\right)\right)},$$

which as usual is a Gamma distribution.

With the above reasoning and derivation, algorithm A4 can be modified accordingly and is described below and with references to the flowcharts of FIG. 3. The modifications occur in the substeps of the Bayesian inference analysis, substeps 810; 1-5 corresponding to step 710: 1-5 of algorithm A4, only. Therefore only these substeps are described below.

Algorithm A7:
  810: 1 The Bayesian inference analysis, step 810 (corresponding to 710) comprises the substeps of:
  810: 1 Initialize:
  810: 1.1 set bin size and position: $d_k$ (k=1, 2, ..., K) (from hardware design)
  810: 1.2 set subbin size and position for each k: $d_{k,j}$ (l=1, 2, ..., $L_k$) (inside $d_k$'s bin)

810: 1.3 count photons in each time bin:

$$c_k = \sum_{n=1}^{N} c_{n,k}$$

810: 1.4 set number of samples required
810: 1.5 select starting value for each $A_i$, options:
  i) select random sample from prior on $A_i$
  ii) select mean from prior on $A_i$
  iii) select mode from prior on $A_i$
  iv) user input data
810: 2 Update B
810: 2.1 For each k(1, 2, ..., K)
810: 2.1.1 Update $b_k$:
set $b_k$ to be a random sample from the multinomial distribution with $$c_k = \sum_{n=1}^{N} c_{n,k}$$

total tosses, $IL_k$ outcomes and toss probability $$\text{EMBED} \frac{w_{k,l} A_i e^{-\alpha_i d_{k,l}} e^{\sum_{i'=1}^{I} \left(\frac{A_{i'}}{\alpha_{i'}}\left(1-e^{-\alpha_{i'}\delta}\right)\sum_{k=1}^{K} e^{-\alpha_{i'} d_{k,l}}\right)}}{\sum_{i=1}^{i} \sum_{l=1}^{L_k} w_{k,l} A_i e^{-\alpha_i d_{k,l}} e^{\sum_{i'=1}^{I} \left(\frac{A_{i'}}{\alpha_{i'}}\left(1-e^{-\alpha_{i'}\delta}\right)\sum_{k=1}^{K} e^{-\alpha_{i'} d_{k,l}}\right)}}$$

(see Appendix)

810: 2.2 Next k
810: 3 Update A $$\text{EMBED}(A, \alpha, B \mid D) \propto \left(\prod_{k=1}^{K} \prod_{l=1}^{L_k} w_{k,l}^{\sum_{i=1}^{I} b_{k,i,l}}\right)$$

$$\left(\prod_{i=1}^{I} A_i^{m_{A_i}-1+\sum_{k=1}^{K}\sum_{l=1}^{L_k} b_{k,i,l}} \alpha_i^{m_{\alpha_i}-1}\right) \cdot e^{-\sum_{i=1}^{I}\left(r_{A_i} A_i + \alpha_i(r_{\alpha_i} + \sum_{k=1}^{K}\sum_{l=1}^{L_k} b_{k,i,l} d_{k,l}) + \frac{A_i}{\alpha_i}\left(N(e^{-\alpha_i \tau}-e^{-\alpha_i \nu})-(1-e^{-\alpha_i \delta})\sum_{k=1}^{K}\sum_{l=1}^{L_k}\left(e^{-\alpha_i d_{k,l}}\sum_{i'=1}^{I} b_{k,i',l}\right)\right)\right)}$$

810: 3.1 For each i(1, 2, ..., I)
810: 3.1.1 Update $A_i$:
810: 3.1.1.1 Calculate $$m = m_{A_i} + \sum_{k=1}^{K} \sum_{l=1}^{L_k} b_{k,i,l}$$

810: 3.1.1.2 Calculate $$r_i = r_{A_i} + \frac{1}{\alpha_i}\left(N(e^{-\alpha_i \tau} - e^{-\alpha_i \nu}) - (1-e^{-\alpha_i \delta})\sum_{k=1}^{K}\sum_{l=1}^{L_k}\left(e^{-\alpha_i d_k}\right)\sum_{i'=1}^{I} b_{k,i',l}\right)$$

810: 3.1.1.3 Set new value of $A_i$ to be a random sample from the Gamma distribution with parameters m,$r_i$ (see Appendix)
810: 3.2 Next i
810: 4 Add value of A to list of samples of A
810: 5 Enough samples? Yes—goto 820, No—repeat 810: 2-5

Just as in the previous algorithm it is possible to reverse the order of updating A and B with slight modifications of the algorithm.

Algorithm A8, Multiple Fluorophore with Unknown Lifetimes and Binning of the Photon Times in Bins and Subbins The principle of binning of the photon arrival times in bins and subbins can be utilized also in the case of multiple fluorophores with unknown lifetimes, which will be illustrated below in an embodiment of the present invention. It can be seen as a generalization of algorithm A7. As before when the lifetimes are unknown, we presume Gamma priors on them. The simplifications that result in the simpler case where ($\forall$k) $L_k$=1 should be obvious.

As enunciated in the description of algorithm A2 above, the posterior here before binning is given by Equation 24

$$P(A, \alpha \mid D) \propto \left(\prod_{i=1}^{I} A_i^{m_{A_i}-1} \alpha_i^{m_{\alpha_i}-1}\right)\left(\prod_{n=1}^{N}\prod_{k=1}^{K_n}\sum_{i=1}^{I} A_i e^{-\alpha_i t_{n,k}}\right)$$

$$e^{-\sum_{i=1}^{I}\left(r_{A_i} A_i + r_{\alpha_i}\alpha_i + \frac{A_i}{\alpha_i}\left(N(e^{-\alpha_i \tau}-e^{-\alpha_i \nu})-(1-e^{-\alpha_i \delta})\sum_{n=1}^{N}\sum_{k=1}^{K_n} e^{-\alpha_i t_{n,k}}\right)\right)}$$

while with binned data and the additional variables, using the notation of the last algorithms, we have Equation 25 under the constraint that for all k we have $$\sum_{l=1}^{L_k}\sum_{i=1}^{I} b_{k,i,l} = \sum_{n=1}^{N} c_{n,k}$$

(and otherwise P(A,$\alpha$,B|D)=0).

It is now easy to write down the conditional distributions:

Equation 26

$$P(A \mid \alpha, B, D) \propto \left(\prod_{i=1}^{I} A_i^{m_{A_i}-1+\sum_{k=1}^{K}\sum_{l=1}^{L_k} b_{k,i,l}}\right)$$

$$e^{-\sum_{i=1}^{I}\left(A_i\left(r_{A_i}+\frac{1}{\alpha_i}\left(N(e^{-\alpha_i \tau}-e^{-\alpha_i \nu})-(1-e^{-\alpha_i \delta})\sum_{k=1}^{K}\left(\sum_{l=1}^{L_k} e^{-\alpha_i d_{k,l}}\sum_{i'=1}^{I} b_{k,i',l}\right)\right)\right)\right)}$$

(which is a product of Gamma distributions);

P(B|A,α,D) is a product of multinomials, with P($b_k$|A,α, D) having toss probabilities Equation 27

$$\text{EMBED} \frac{w_{k,l} A_i e^{-\alpha_i d_{k,l}} e^{\sum_{i'=1}^{I} \left(\frac{A_{i'}}{\alpha_{i'}}(1-e^{-\alpha_{i'}\delta})\sum_{k=1}^{K} e^{-\alpha_{i'} d_{k,l}}\right)}}{\sum_{i=1}^{I} \sum_{l=1}^{L_k} w_{k,l} A_i e^{-\alpha_i d_{k,l}} e^{\sum_{i'=1}^{I} \left(\frac{A_{i'}}{\alpha_{i'}}(1-e^{-\alpha_{i'}\delta})\sum_{k=1}^{K} e^{-\alpha_{i'} d_{k,l}}\right)}}$$

and total tosses $$\sum_{n=1}^{N} c_{n,k};$$

while finally

Equation 28

$$P(A, \alpha | B, D) \propto \left( \prod_{i=1}^{I} A_i^{m_{A_i}-1+\sum_{k=1}^{K}\sum_{l=1}^{L_k} b_{k,i,l}} \alpha_i^{m_{\alpha_i}-1} \right)$$

$$e^{-\sum_{i=1}^{I} \left( r_{A_i} A_i + \alpha_i (r_{\alpha_i} + \sum_{k=1}^{K}\sum_{l=1}^{L_k} b_{k,i,l} d_{k,l}) + \frac{A_i}{\alpha_i}\left(N(e^{-\alpha_i \tau} - e^{-\alpha_i \nu}) - (1-e^{-\alpha_i \delta})\sum_{k=1}^{K}\left(\sum_{l=1}^{L_k} e^{-\alpha_i d_{k,l}} \sum_{i'=1}^{I} b_{k,i',l}\right)\right)\right)}$$

$$\therefore P(\alpha | B, D) \propto \int P(A, \alpha | B, D) dA$$

$$= \prod_{i=1}^{I} \frac{\alpha_i^{m_{\alpha_i}-1} e^{-\alpha_i (r_{\alpha_i} + \sum_{k=1}^{K}\sum_{l=1}^{L_k} b_{k,i,l} d_{k,l})} \Gamma\left(m_{A_i} + \sum_{k=1}^{K}\sum_{l=1}^{L_k} b_{k,i,l}\right)}{\left(r_{A_i} + \frac{1}{\alpha_i}\left(N(e^{-\alpha_i \tau} - e^{-\alpha_i \nu}) - (1-e^{-\alpha_i \delta})\sum_{k=1}^{K}\left(\sum_{l=1}^{L_k} e^{-\alpha_i d_{k,l}} \sum_{i'=1}^{I} b_{k,i',l}\right)\right)\right)^{m_{A_i} + \sum_{k=1}^{K}\sum_{l=1}^{L_k} b_{k,i,l}}}$$

where of course the Gamma functions do need to be calculated as they are not constants.

Given these three conditional distributions, we can now in principle resample as follows. For odd j we now draw a sample for $B_{j+1}$ from a multinomial distribution with the multi-way toss probabilities defined above, while for even j we resample ($A_{j+i}$, $\alpha_{j+1}$) (α is a vector) by first sampling α from the marginal conditional P($\alpha_{j+1}$, |$B_{j+1}$, D), and then sampling $A_{j+1}$ from the conditional distribution P($A_{j+1}$|$\alpha_{j+1}$, $B_{j+1}$,D).

The only part of the this procedure that has so far not been fully defined is the step of resampling from P($\alpha_{j+1}$|$B_{j+1}$,D). This will be expanded below.

With the above reasoning and derivation, algorithm A7 can be modified accordingly and is described below and with references to the flowcharts of FIG. 3. The modifications of importance occur in the substeps of the Bayesian inference analysis, substeps 910: 1-4 corresponding to substeps 810: 1-4 of algorithm A4, only. Therefore only these substeps are described below.

Algorithm A8:
910: The Bayesian inference analysis, step 910 (corresponding to 810) comprises the substeps of:
910: 1 Initialize:
910: 1.1 set bin size and position: $d_k$ (k=1, 2, ..., K) (from hardware design)
910: 1.2 set subbin size and position for each k: $d_{k,l}$ (l=1, 2, ..., $L_k$) (inside $d_k$'s bin)
910: 1.3 count photons in each time bin:

$$c_k = \sum_{n=1}^{N} c_{n,k}$$

910: 1.4 set number of samples required
910: 1.5 set both $r_{A_i}$, $m_{A_i}$ and $r_{\alpha_i}$, $m_{\alpha_i}$ in one of the same ways that $r_{A_i}$, $m_{A_i}$ were set in algorithm A4.
910: 2: For each j:
910: 2.1 If j is odd: Update B.
910: 2.1.1 For each k(1, 2, ..., K)
910: 2.1.1.1 Update $b_k$:
set $b_k$ to be a random sample from the multinomial distribution with $$c_k = \sum_{n=1}^{N} c_{n,k}$$

total tosses, I$L_k$ outcomes and toss probabilities $$\text{EMBED} \frac{w_{k,l} A_i e^{-\alpha_i d_{k,l}} e^{\sum_{i'=1}^{I} \left(\frac{A_{i'}}{\alpha_{i'}}(1-e^{-\alpha_{i'}\delta})\sum_{k=1}^{K} e^{-\alpha_{i'} d_{k,l}}\right)}}{\sum_{i=1}^{I} \sum_{l=1}^{L_k} w_{k,l} A_i e^{-\alpha_i d_{k,l}} e^{\sum_{i'=1}^{I} \left(\frac{A_{i'}}{\alpha_{i'}}(1-e^{-\alpha_{i'}\delta})\sum_{k=1}^{K} e^{-\alpha_{i'} d_{k,l}}\right)}}$$

(see Appendix)

910: 2.1.2 Next k
910: 2.2 If j is even:
910: 2.2.1 Resample ($A_{j+1}$, $\alpha_{j+1}$) by
910: 2.2.1.1 Sampling α from P($\alpha_{j+1}$|$B_{j+1}$,D) (eq. 28) (see below for description of how this is done)
910: 2.2.1.2 Sampling $A_{j+1}$, from P($A_{j+1}$|$\alpha_{j+1}$,$B_{j+1}$,D) (eq.26)
910: 2.2.2 Add A to list of samples of A
910: 3 next j:
910: 4 Enough samples? Yes—goto 920, No—repeat 910: 2-4

Sampling α from P($\alpha_{j+1}$|$B_{j+1}$,D) (in step 935) is not obvious. Below a suitable method, readily converted into program code, is outlined.

Resampling from the conditional for a can be performed as follows: We introduce a Markov Chain Monte Carlo (MCMC) technique whose proposal distribution is not a conditional distribution, does depend on the previous sample and does not always accept the new sample.

Suppose then that we have values of $B_{j+1}$, and D, and also the previous value of the ith component of α namely $α_{j,i}$ (we now have two subscripts in order to indicate both which sample and which component). Note that the conditional distribution of P(α|B,D) is separable over i, so that we can treat each component separately. Let the current conditional distribution $P(α_i|B,D)$ be denoted $f(α_i)$, so that $$f(α_i) \propto \frac{α_i^{m_{α_i}-1} e^{-α_i(r_{α_i} + \sum_{k=1}^{K} \sum_{l=1}^{L_k} b_{k,i,l} d_{k,l})} \Gamma\left(m_{A_i} + \sum_{k=1}^{K} \sum_{l=1}^{L_k} b_{k,i,l}\right)}{\left(r_{A_i} + \frac{1}{α_i}\left(N(e^{-α_i τ} - e^{-α_i ν}) - (1 - e^{-α_i δ}) \sum_{k=1}^{K}\left(\sum_{l=1}^{L_k} e^{-α_i d_{k,l}} \sum_{i'=1}^{l} b_{b,i',l}\right)\right)\right)^{m_{A_i} + \sum_{k=1}^{K} \sum_{l=1}^{L_k} b_{k,i,l}}}$$

Equation 29

Then the overall move in ai needs to satisfy detailed balance with respect to this distribution. It is easy to show that if it does, then the alternating sequence of moves described before will also hold detailed balance over every subsequence of three moves, and hence that the necessary conditions for our MCMC process will be met.

It is also easy to show that if we have two potential types of move that each holds detailed balance with respect to this distribution, then so also will a compound move that proceeds by choosing one of these two types at random (with any fixed probabilities) and applying it. We now then go on to describe two types of move, which we will use with some fixed probabilities (for example 0.5 and 0.5) whenever a move to resample $α_i$ is required.

Both types of move involve sampling a proposed value α' from a proposal distribution $g(α'|α_{j,i})$, dependent on the previous value of $α_i$, namely $α_{j,i}$, followed by a probabilistic decision either to accept α' (in which case we set $a_{j+1,i}=α'$) or to reject it (in which case we set $α_{j+1,i}=α_{j,i}$). In both cases we accept with probability $$p_α = \frac{f(α')g(α_{j,i}|α')}{f(α_{j,i})g(α'|α_{j,i})}.$$

Equation 30

All that remains then is to define the two proposal distributions, one for each type of move.

Proposal Distribution 1—"The Coarse Grid":

Let $α_{j,i}$ be given; fix also (once and for all) some parameters γ and H, where γ is a positive real number (20 will do) and H is a positive integer (again, 20 will do). Then let $X_1$ be the set $$\{x_h = α_{j,i} γ^{\frac{h}{H}} : h \in \{-H, -H+1, ..., H-1, H\}\},$$

and let $g_1(α'|α_{j,i})$ be the unique (discrete) probability distribution on $X_1$ that is proportional to f(x).

Proposal Distribution 2—"The Fine Fill-In":

Using the same parameters γ and H, let $X_2$ be the closed interval $$\left[α_{j,i} γ^{-\frac{1}{H}}, α_{j,i} γ^{+\frac{1}{H}}\right],$$

and let $g_2(α'|α_{j,i})$ be the unique (continuous) probability distribution on $X_2$ that is proportional to $$\frac{1}{x}.$$

The measurement system with the capability of detecting and recording multiple photons after one excitation in combination with the method of the present invention, the essence of which is implementing Bayesian inference in the algorithms executed during each measurement, represents a significant improvement in measurement speed over the prior art techniques. The inventive method of, in each measurement, inferring the source (i.e. the originating fluorophore) of each photon, further shortens the measurement time (algorithm A3). In Table 1 a comparison is given of the measurement times of four different dyes (having different lifetimes) using the TCSPC and the TCMPC techniques. The same solutions were used with both instruments. These numbers are only indicative, but show a faster speed for the TCMPC technique.

TABLE 1

Measurement time with different dyes using TCSPC and TCMPC, respectively.

| Lifetime of the Dye | Time to run the experiment(s) | |
|---|---|---|
| | TCSPC | TCMPC |
| 4 ns | 493 | 9.94 |
| 8 ns | 28 | 9.55 |
| 14 ns | 196 | 18.79 |
| 20 ns | 640 | 13.35 |

In the described method according to the present invention, the fluorescence decay of a fluorophore bound to a biological molecule has been modelled by a mono-exponential decay or in some cases a bi-exponential decay. However, there are situations in which one does not expect a limited number of discrete decay times but rather a distribution of decay times. In complex heterogeneous biological systems, multi-exponential decays functions can appear to provide a better fit of the fluorescence decay data than the assumption of a mono-exponential decay. But the assumption of multiple discrete components is essentially arbitrary and is often erroneous. For example, for a single tryptophan protein, the distribution of decay time may reflect the distribution of protein conformation, alternatively it could be a protein with many tryptophan residues, so it is not practical to consider the individual decay times. Moreover, interaction between the fluorophore and the environment can result in complex fluorescence decay profiles that represent a continuous distribution of lifetimes. A method according to the present invention may also account for such cases.

The intensity decays λ(t) may be analysed in terms of a lifetime distribution $ρ(τ_l$, wherein $τ_l/1α$ and α is the decay constant. The total decay law becomes:

$$\lambda(t) = \int_{\tau=0}^{\infty} \rho(\tau_l) e^{\frac{t}{\tau_l}} \cdot d\tau_l \qquad \text{equation 31}$$

The fluorescence decay of biological systems may in some cases advantageously be described by a so-called stretched exponential as the stretched exponential reflects a continuous distribution of fluorescence lifetimes. The stretched exponential is introduced by:

$$\lambda(t) = A_0 \cdot e^{-\left(\frac{t}{\tau_1}\right)^{\frac{1}{h}}} \qquad \text{equation 32}$$

where h is called the heterogeneity and is related to the distribution of decay times. In the case of a mixture of both substrate and product, each contributing to the fluorescence decay, a sum of two stretched exponentials may be used:

$$\lambda(t) = A_1 \cdot e^{-\left(\frac{t}{\tau_{l_1}}\right)^{\frac{1}{h_1}}} + A_2 \cdot e^{-\left(\frac{t}{\tau_{l_2}}\right)^{\frac{1}{h_2}}} \qquad \text{equation 33}$$

The stretched exponential model may advantageously be combined with the analysis using Bayesian inference according to the present invention which has been exemplified in the algorithms A1-A8. For example algorithm A1, taking into account the various deadtimes and utilizing the stretched exponential model may be modified as described below.

The Poisson arrival rate of the photons at time t is denoted by λ(t) as described by equation 32. The equations of algorithm A1 (equation 11-13) should be modified accordingly by using the following expression for the likelihood of observing the data $D_n$:

$$P(D_n \mid A_0, \tau, h) = \qquad \text{equation 34}$$
$$\left(\prod_{k=1}^{K_n} (\lambda(t_{n,k}))\right) e^{-\left(\int_\tau^\nu \lambda(t_{n,k}) dt - \sum_{k=1}^{K_n} \int_{t_{n,k}}^{t_{n,k}+\delta} \lambda(t_{n,k}) dt\right)}$$

where the detector is dead for a duration δ after each photon is received, for a duration τ after the excitation, and at all times longer than υ after excitation. $K_n$ is the number of photons received following the $n^{th}$ laser pulse and $t_{n,k}$ is the arrival of the $k^{th}$ photon from laser pulse n. Furthermore, the expression for prior probability distribution should be modified accordingly to included any prior knowledge on the values of the heterogeneity parameter h. Also the other algorithms, including the algorithms using binning of photon arrival times (A4-A8), may in the same way be modified to include stretched exponentials.

The inventive method, exemplified with algorithms A1-A8, has been described here in combination with the measurement system comprising the photodetector 160 and the photon timing unit 150 having the ability to detect and output multiple photon arrival times after each excitation light pulse from the pulsed laser 120. This is considered to be the best mode of operation. However, as appreciated by those skilled in the art, parts of the method of the present invention can advantageously be used also with prior art apparatuses such as the TCSPC and Multiplexed-TCSPC, providing only one (TCSPC) or a limited (Multiplexed-TCSPC) number of photons per excitation pulse.

The inventive method and measurement system has been exemplified here with fluorophores. As appreciated by those skilled in the art the system and methods are equally applicable in characterising other luminescent substances e.g. phosphorescent materials.

Example of luminescent substances that can advantageously be analysed with the described method and system comprises fluorescent materials (which usually have short lifetimes, typically of the order of <1 ns-100 ns) e.g. Fluorescein, CyDyes, and ethidium bromides; and Phosphorescent material (which usually have longer lifetimes (typically a few ms)) e.g. ruthenium chelates, terbium chelates.

From the invention thus described, it will be obvious that the invention may be varied in many ways. Such variations are not to be regarded as a departure from the scope of the invention, and all such modifications as would be obvious to one skilled in the art are intended for inclusion within the scope of the following claims.

APPENDIX

A method of drawing random samples from a Gamma distribution and from a multinomial distribution, respectively, will be given below. The description will be in the form of guidelines which the skilled programmer can easily convert into subroutines suitable to call from algorithms A3-A8.

Random Samples from a Gamma Distribution

The Gamma distribution is defined by $$\Gamma_{m,r}(x) = \frac{r^m x^{m-1} e^{-rx}}{\Gamma(m)}$$

as described above. Obtaining a random sample from it can be done in many ways. The best known currently to the inventors proceeds differently depending on whether m is less than 1, equal to 1, or greater than 1. Whichever is being used, we can initially assume that r=1 and then divide the resulting sample by r afterwards.

The Easy Case: m=1

In this case the distribution reduces to an exponential distribution. The cumulative distribution function is therefore $$P(x \leq y) = 1 - e^{-y}$$

and we may therefore choose a uniformly distributed random number u from the interval [0, 1] and solve the equation $u = 1 - e^{-y}$ for y which we output as our random sample.

The Difficult Cases: m<1 and m>1

For both of these cases we use forms of rejection sampling.

Suppose we want to sample from a probability distribution f(x) and are already able to sample from a probability distribution g(x). Suppose moreover that there exists a constant K such that for all x we have $Kf(x) \leq g(x)$. Then it is easy to see that the following algorithm will result in a sample from f(x) with probability K and with the remaining probability will result in no sample:

Draw a random sample y from g(x).

With probability Kf(x)/g(x) let y be the resultant sample, and with the remaining probability let there be no resultant sample.

If, therefore, we keep applying this algorithm until it does yield a sample, then we will end up with a sample from f(x) with probability $1-(1-K)^N$ after N repeats. Since this probability approaches 1 as N approaches infinity, we will eventually end up with a sample with probability 1.

All that remains now is to specify g(x) for each of the relevant cases, state how to draw samples from g(x), and how to calculate Kf(x)/g(x).

m>1 g(x) is given by $$g(x) = \frac{c}{2(c+(x-b)^2)^{3/2}} \text{ where } b = m-1 \text{ and } c = 3b + \frac{9}{4}.$$

The cumulative density function is given by $$P_g(x<y) = \frac{1}{2}\left(1 \pm \sqrt{1 - \frac{c}{c+(y-b)^2}}\right)$$

where the positive sign is taken if y>b and the negative sign otherwise. We can therefore draw randomly from g(x) by drawing u randomly from the interval [0, 1], solving $$u = \frac{1}{2}\left(1 \pm \sqrt{1 - \frac{c}{c+(y-b)^2}}\right) \text{ for } y,$$

and making y be our random sample from g(x).

Now, let $$h(x) = \frac{g(x)}{f(x)},$$

so that $$h(x) = \frac{\frac{c}{2(c+(x-b)^2)^{3/2}}}{\frac{x^{m-1}e^{-x}}{\Gamma(m)}}$$

$$= \frac{c\Gamma(m)e^x}{2x^{m-1}(c+(x-b)^2)^{3/2}}$$

and this is therefore minimised where $$0 = h'(x) = \frac{c\Gamma(m)e^x}{2x^{m-1}(c+(x-b)^2)^{3/2}}\left(1 - \frac{m-1}{x} - \frac{3(x-b)}{c+(x-b)^2}\right)$$

which is where the final factor is zero, or $$0 = 1 - \frac{m-1}{x} - \frac{3(x-b)}{c+(x-b)^2}$$

$$\therefore x(c+(x-b)^2) - (m-1)(c+(x-b)^2) - 3(x-b)^2 = 0$$

$$\therefore (x-b)(c+(x-b)^2) - 3(x-b)^2 = 0$$

$$\therefore (x-b)(c+(x-b)^2 - 3(x-b)) = 0$$

$$\therefore (x-b)\left((x-b)^2 - 3(x-b) + \left(3b + \frac{9}{4}\right)\right) = 0$$

The second factor has a negative discriminant since b>0, and can therefore never be zero and is always positive; the only extremum of h(x) is therefore at x=b and is a minimum; at that point we have $$K = \min_x h(x) = h(b) = \frac{c\Gamma(m)e^b}{2b^{m-1}(c+(b-b)^2)^{3/2}} = \frac{\Gamma(m)e^b}{2b^bc^{1/2}},$$

so the acceptance probability for the sample can be set at $$p_a(x) = Kf(x)/g(x)$$

$$= \frac{\Gamma(m)e^b}{2b^bc^{1/2}} \frac{2x^{m-1}(c+(x-b)^2)^{3/2}}{c\Gamma(m)e^x}$$

$$= \frac{e^b}{b^bc^{3/2}}x^b(c+(x-b)^2)^{3/2}e^{-x}$$

Finally, we note that we will implement the acceptance decision by drawing a uniformly distributed random number v from the interval [0, 1], and accepting our random sample if $v < P_\alpha(x)$. The test for whether $v < p_\alpha(x)$ or not can be speeded up in many instances by testing first whether v is less than some other function of x that is simpler to calculate and which is always less than $p_\alpha(x)$, and accepting the sample if it is.

m<1

In this case we set $$g(x) = \begin{cases} \frac{mx^{m-1}t}{t^m(t+m e^{-t})} & \text{if } 0 \leq x \leq t \\ \frac{me^{-x}}{t+me^{-t}} & \text{if } x > t \\ 0 & \text{otherwise} \end{cases}$$

where t=1−m.

The cumulative density function is $$P_g(x<y) = \begin{cases} \frac{y^m t}{t^m(t+me^{-t})} & \text{if } 0 \leq y \leq t \\ 1 - \frac{me^{-y}}{t+me^{-t}} & \text{if } y > t \\ 0 & \text{otherwise} \end{cases}$$

and we can therefore draw a random sample from g(x) by drawing a uniformly distributed random number u from the interval [0, 1] and solving $P_g(x<y)=u$ for y.

Similarly to the derivation in the previous section, we can now set $$h(x) = \frac{g(x)}{f(x)} = \begin{cases} \frac{mt\Gamma(m)e^x}{t^m(t+me^{-t})} & \text{if } 0 \leq x \leq t \\ \frac{m\Gamma(m)x^t}{t+me^{-t}} & \text{if } x > t \end{cases}$$

The minima of both continuous sections are at the left hand end of the section, i.e.

$$\arg\min_{x\in I} g(x) = \begin{cases} 0 & \text{if } I = [0, t] \\ t+ & \text{if } I = (x, t] \end{cases}$$

and are therefore at $$K = \frac{\Gamma(m)mt}{t^m(t + me^{-t})}$$

in both cases.

Therefore the acceptance probability $$p_a(x) \text{ is } e^{-y} \text{ if } y \le t \text{ or } \left(\frac{y}{t}\right)^{m-1} \text{ if } y > t.$$

Finally, we note that we will implement the acceptance decision by drawing a uniformly distributed random number v from the interval [0, 1], and accepting our random sample if $v < p_a(x)$. The test for whether $v < p_a(x)$ or not can be rearranged by first calculating $$w = \begin{cases} x & \text{if } x \le t \\ t \log\left(\frac{x}{t}\right) & \text{if } x > t \end{cases}$$

then testing whether $v < e^{-w}$. This test can then be speeded up in many instances by first testing whether $$v > \frac{1}{1+w}$$

(in which case we reject the sample and try all over again), or whether $v < 1-w$ (in which case we accept the sample and have finished), and only if we reach this point do we then have to test whether $v < e^{-w}$.

Random Samples from a Multinomial Distribution

We finally turn to efficient methods for sampling from a multinomial distribution.

The multinomial distribution is analagous to the binomial distribution, but for tosses where there are more than 2 possible outcomes. The parameters are N, the total number of tosses, and p, the vector of probabilities for the different possible results of a toss. The distribution is given by $$P(n \mid N, p) = \frac{N!}{\prod_{i=1}^{I} n_i!} \prod_{i=1}^{I} p_i^{n_i}.$$

Converting Production of a Single Multinomial Random Sample Into a Sequence of Binomial Ones The best way known to the author for sampling from this distribution is to convert the problem into a sequence of binomial random samples. The first determines the values of $n_1$ and $$\sum_{i=2}^{I} n_i,$$

using as parameters for the binomial draw N and $p_1$. The kth determines the values of $n_k$ and $$\sum_{i=k+1}^{I} n_i,$$

using as parameters for the binomial draw $$N - \sum_{i=1}^{k-1} n_i$$

and $p_k$. That leaves the question of how to efficiently produce a binomial random sample.

Production of Binomial Random Samples

The binomial distribution is the special case of the multinomial distribution where I=2, except that usually (including here) the 2-element parameter vector p is presented as the single element $p = p_1$ (which uniquely determines p since the elements of the latter must sum to 1).

The best way known to the inventors for sampling from the binomial distribution is to first order the values of $$q_n = \frac{N!}{(N-n)!} p^n (1-p)^{N-n}$$

in descending order (conceptually, without actually calculating them all), then to draw a uniformly distributed random number x from the range [0, 1], then to subtract from x in succession the values of $q_n$ in succession starting with the largest. The output value n is the index of the $q_n$ which takes the remaining amount left in x below zero.

Implementation of this can take advantage of the fact that the method works almost as well if the $q_n$ are used in a slightly different order from the optimal one. We can therefore safely assume that $$\arg\max_{n}(q_n) = \text{round}(Np),$$

and calculate this $q_n$ first. Each subsequent one can then be calculated in order from either the one before or the one after it in succession.

What is claimed is:

1. A method for determining one or more characteristics of a fluorophore material, the method comprising the steps of:
   a) irradiating the fluorophore material with a pulse of excitation light from a single light source;
   b) providing a triggering signal correlated to the pulse of excitation light;
   c) detecting with a single photomultiplier tube (PMT), a plurality of photons emitted from the fluorophore material as result of the pulse of excitation light, the single PMT providing an output signal that represents the plurality of photons detected by the single PMT;

d) determining for each detected photon a photon, in the plurality of photons detected by the single PMT, arrival time and providing an output suitable for inputting to an analysing module wherein an output comprises zero, one, or more photon arrival times for each excitation;

e) repeating steps a) to d) until a predetermined number of excitations has been performed;

f) receiving said outputs in an analysing module;

g) determining, in the analysing module, characteristic properties of the fluorophore material by performing a probabilistic analysis based on Bayesian inference that does not provide spatial resolution; and wherein performing the probabilistic analysis based on Bayesian inference comprises taking into account a first time period ($\delta$) describing a photomultiplier tube (PMT) dead time; a second time period ($\tau$) describing blocking of the photodetector after an excitation; and a third time period ($\upsilon$) describing the duration of recording after each excitation; and h) providing an output of the probabilistic analysis based on the Bayesian inference to a computer.

2. The method of claim 1, wherein the fluorophore material is selected based on a fluorescence lifetime of the fluorophore material, an initial intensity of the fluorophore material, and ratios of fluorescence initial intensities.

3. The method of claim 1, wherein performing probabilistic analysis based on the Bayesian inference comprises determining the fluorophore material from which each detected photon originates.

4. The method of claim 1, wherein performing probabilistic analysis based on the Bayesian inference comprises including experimental artefacts in the Bayesian inference.

5. The method of claim 1, wherein steps a) to g) are repeated until statistical uncertainties of the measured properties are below predefined values or until a predetermined number of repetitions of steps a) to g) have been performed.

6. The method of claim 1, wherein performing probabilistic analysis based on the Bayesian inference further comprises also inferring in which part of a time bin the true arrival time of each photon lies.

7. A measurement system for measuring luminescence characteristic properties of a fluorophore material, comprising a light source driving and controlling unit; and an excitation light source for irradiating the fluorophore material with pulses of excitation light, said light source driving and controlling unit providing a triggering signal correlated to each pulse of excitation light;

a single photomultiplier tube (PMT), for detecting a plurality of photons emitted from the fluorophore material as result of a single pulse of excitation light, said single PMT providing an amplified output signal that represents the plurality of photons detected by the single PMT;

means for photon timing determination coupled to receive said amplified output signal and said triggering signal, the means for photon timing determination determining for each emitted photon in the plurality of photons detected by the single PMT, a photon arrival time and providing an output of a plurality of photon arrival times, and means for analysing the plurality of photon arrival times, arranged to receive said plurality of photon arrival times outputted from said means from photon timing determination, and able to determine from the plurality of photon arrival times characteristic properties for the fluorophore material, wherein the photon timing determination means determines and stores a plurality of arrival time measures corresponding to a plurality of detected photons, the plurality of photons resulting from the same pulse of excitation light; and wherein said means for analysing the plurality of photon arrival times, utilises an algorithm for the determination of characteristic fluorescent properties of the fluorophore material that is based on Bayesian inference; and wherein the algorithm for the determination of characteristic luminescent properties of the fluorophore material based on the Bayesian inference includes a first time period ($\delta$) describing a PMT dead time; a second time period ($\tau$) describing blocking of the photodetector after an excitation; and a third time period ($\upsilon$) describing the duration of recording after each excitation.

8. The measurement system of claim 7, wherein said means for analysing the plurality of photon arrival times is capable of performing probabilistic analysis based on the Bayesian inference and inferring in which a time bin the true arrival time of each photon lies.

9. The measurement system of claim 7, wherein said photon timing determination means is arranged to record a signal from a pre-amplifier at a sampling frequency above 1 GHz.

10. The method of claim 1 wherein detecting with a single photodetector further comprises detecting with a single photodetector forming a portion of a photodector array, a plurality of photons emitted from the fluorophore material as result of the pulse of excitation light, the photodector array including a plurality of photodectors, each photodetector detecting a plurality of photons emitted from the fluorophore material as result of the pulse of excitation light.

11. The method of claim 1 wherein detecting with a single photodetector further comprises detecting with a photon counting photomultiplier tube (PMT) a plurality of photons emitted from the fluorophore material as result of the pulse of excitation light.

* * * * *